(12) United States Patent
Boyle et al.

(10) Patent No.: US 11,779,317 B2
(45) Date of Patent: Oct. 10, 2023

(54) SURGICAL DEVICE CONFIGURED TO STRIP AND CUT TENDON

(71) Applicant: ARTHREX, INC., Naples, FL (US)

(72) Inventors: Justin Boyle, Naples, FL (US); Joshua Best, Naples, FL (US); Jacob Jolly, Naples, FL (US); Kenneth T. Helenbolt, Naples, FL (US)

(73) Assignee: ARTHREX, INC., Naples, FL (US)

( * ) Notice: Subject to any disclaimer, the term of this patent is extended or adjusted under 35 U.S.C. 154(b) by 165 days.

(21) Appl. No.: 17/195,911

(22) Filed: Mar. 9, 2021

(65) Prior Publication Data

US 2022/0287695 A1   Sep. 15, 2022

(51) Int. Cl.
*A61B 17/32* (2006.01)
*A61B 17/00* (2006.01)

(52) U.S. Cl.
CPC ........ *A61B 17/00008* (2013.01); *A61B 17/32* (2013.01); *A61B 2017/32006* (2013.01); *A61B 2017/320052* (2013.01)

(58) Field of Classification Search
CPC .............. A61B 17/00008; A61B 17/32; A61B 2017/320052; A61B 1/0008
See application file for complete search history.

(56) References Cited

U.S. PATENT DOCUMENTS

| | | |
|---|---|---|
| 3,844,272 A | 10/1974 | Banko |
| 3,902,498 A | 9/1975 | Niederer |
| 4,773,417 A | 9/1988 | Moore et al. |
| 5,324,298 A | 6/1994 | Phillips et al. |
| 5,391,169 A | 2/1995 | McGuire |
| 5,505,210 A | 4/1996 | Clement |
| 5,522,827 A | 6/1996 | Combs et al. |
| 5,681,314 A | 10/1997 | Derouin et al. |
| 5,911,730 A | 6/1999 | McGuire |
| 6,045,561 A | 4/2000 | Marshall et al. |
| 6,110,190 A | 8/2000 | Ginn et al. |
| 7,163,547 B2 | 1/2007 | Majlessi |
| 7,320,687 B2 | 1/2008 | Lee |
| 7,632,289 B2 | 12/2009 | Majlessi |
| 8,177,803 B2 | 5/2012 | Heisler |
| 8,480,696 B2 | 7/2013 | Clague et al. |
| 8,545,485 B2 | 10/2013 | Merced-O'Neill |

(Continued)

FOREIGN PATENT DOCUMENTS

| | | |
|---|---|---|
| CN | 201248741 | 6/2009 |
| CN | 103006277 A | 4/2013 |

(Continued)

OTHER PUBLICATIONS

Xerogeanes, John, MD, "Quad Tendon Harvest System," Surgical Technique. www.arthrewx.com/corporate/virtual-patent-marketing. 2015.

(Continued)

*Primary Examiner* — Brooke Labranche
*Assistant Examiner* — James R McGinnity
(74) *Attorney, Agent, or Firm* — Carlson, Gaskey & Olds, P.C.

(57) ABSTRACT

The disclosure relates to a surgical device configured to both strip and cut a tendon. The harvested tendon can be used in various orthopedic procedures, such as ACL, PCL, and UCL reconstructions.

17 Claims, 14 Drawing Sheets

(56) References Cited

U.S. PATENT DOCUMENTS

| | | | |
|---|---|---|---|
| 8,864,809 B2* | 10/2014 | Miles | A61B 17/12172 |
| | | | 606/139 |
| 8,894,672 B2 | 11/2014 | Burroughs, III | |
| 8,894,675 B2 | 11/2014 | Burroughs, III | |
| 8,894,676 B2 | 11/2014 | Burroughs, III | |
| 9,044,260 B2 | 6/2015 | Burroughs, III | |
| 9,107,700 B2 | 8/2015 | Burroughs, III | |
| 9,474,535 B2 | 10/2016 | Burroughs, III | |
| 9,763,651 B2 | 9/2017 | Hsiao et al. | |
| 9,808,275 B2 | 11/2017 | Taylor | |
| 10,507,012 B2 | 12/2019 | Knighton et al. | |
| 2004/0087967 A1* | 5/2004 | Schur | A61B 17/00008 |
| | | | 606/108 |
| 2005/0004586 A1 | 1/2005 | Suval | |
| 2006/0149267 A1 | 7/2006 | Nordt | |
| 2007/0106310 A1 | 5/2007 | Goldin et al. | |
| 2009/0048485 A1 | 2/2009 | Heisler | |
| 2009/0264871 A1 | 10/2009 | Merced-O'Neill | |
| 2010/0069944 A1 | 3/2010 | Murakami et al. | |
| 2010/0305594 A1 | 12/2010 | Opie | |
| 2013/0331877 A1 | 12/2013 | Burroughs, III | |
| 2014/0277020 A1 | 9/2014 | Koogle et al. | |
| 2015/0045823 A1 | 2/2015 | Burroughs, III | |
| 2015/0282964 A1* | 10/2015 | Beard | A61F 2/966 |
| | | | 623/1.11 |
| 2016/0270771 A1* | 9/2016 | Hsiao | A61B 17/32053 |
| 2017/0311789 A1* | 11/2017 | Mulcahey | A61B 1/126 |
| 2020/0060663 A1* | 2/2020 | Jolly | A61B 17/32053 |

FOREIGN PATENT DOCUMENTS

| | | |
|---|---|---|
| DE | 19754779 A1 | 6/1999 |
| EP | 0362316 A1 | 4/1990 |
| FR | 2824467 A1 | 11/2002 |
| JP | 2920167 B1 | 7/1999 |
| WO | 8907913 A1 | 9/1989 |
| WO | 2005069924 A2 | 8/2005 |
| WO | 2006119238 A2 | 11/2006 |

OTHER PUBLICATIONS

Storz, Karl. "Minimally Invasive Quadriceps Tendon Harvesting System," EndoWorld, Art 52 4.1 Nov. 2015-E, Karl Storz Endoscopy-America, Inc. 2015.

Stryker, Joint Preservation, "Flexibility in Action," ACL Tunnel-Preparation Instrumentation Set. Literature No. 1000-900-341E rev.1. Jun. 2008.

International Search Report & Written Opinion for International Application No. PCT/US2019/035699 dated Aug. 27, 2019.

Noronha, J.C. (2002). Reconstruction of the anterior cruciate ligament with quadriceps tendon. Sep. 7, 2002. pp. 1-5.

Staubli, H.U. (1997). The quadriceps tendon-patellar bone construct for ACL reconstruction*. Sep. 9, 1998. pp. 126-139.

Franceschi, F., Longo U.G., Ruzzini L., Papalia R., Maff Ulli, N., and Denaro, V. (2008). Quadriceps tendon-patellar bone autograft for anterior cruciate ligament reconstruction: a technical note. Feb. 2008. pp. 119-123.

Fulkerson, J.P., McKeon, B.P., Donahue, B.J, and Tarinelli, D.J. (1998). The central quadriceps tendon as a versatile graft alternative in anterior cruciate ligament reconstruction: techniques and recent observations. Dec. 1998. pp. 367-374.

International Search Report and Written Opinion for PCT Application PCT/US2022/016061 dated May 24, 2022.

* cited by examiner

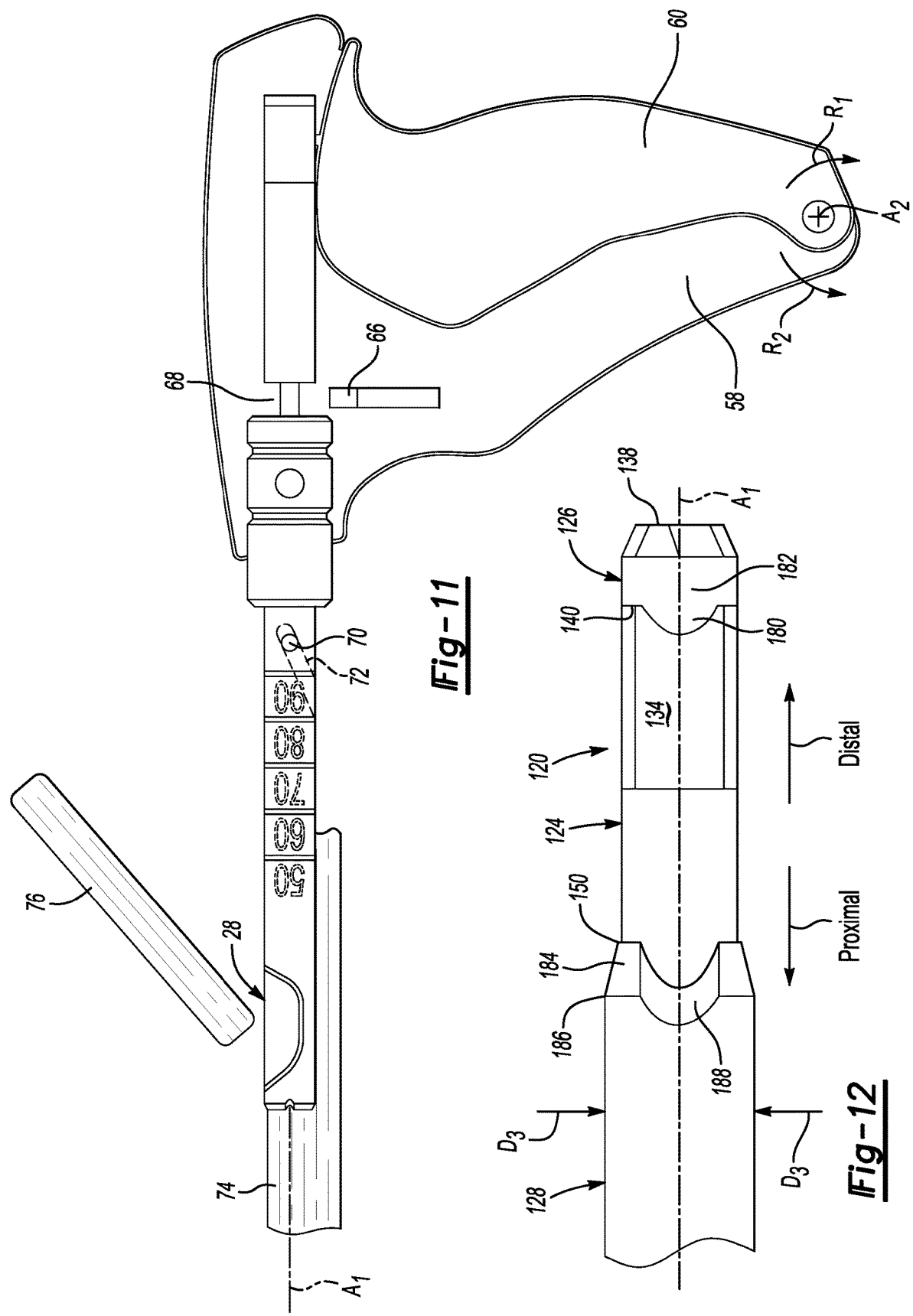

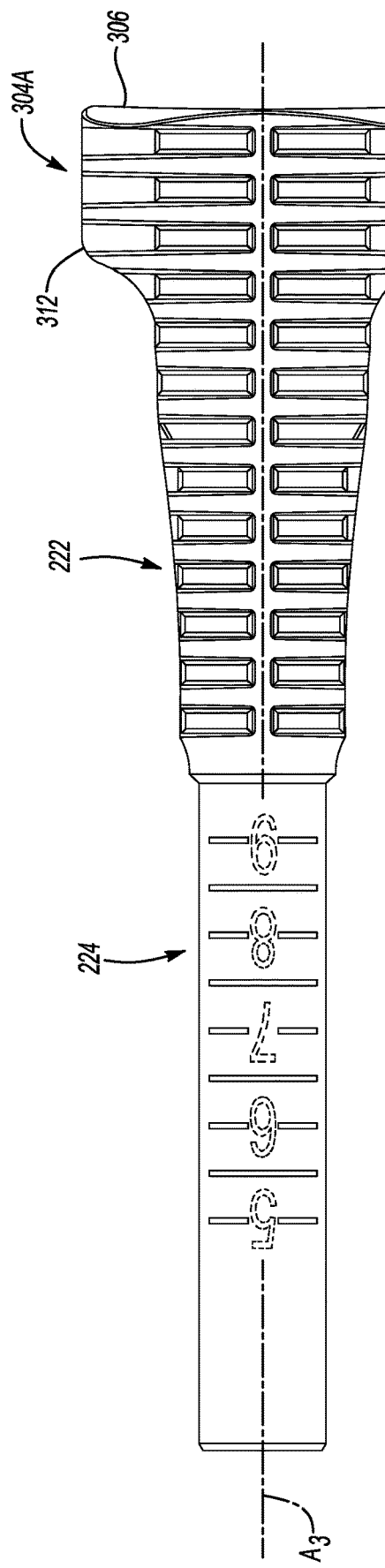
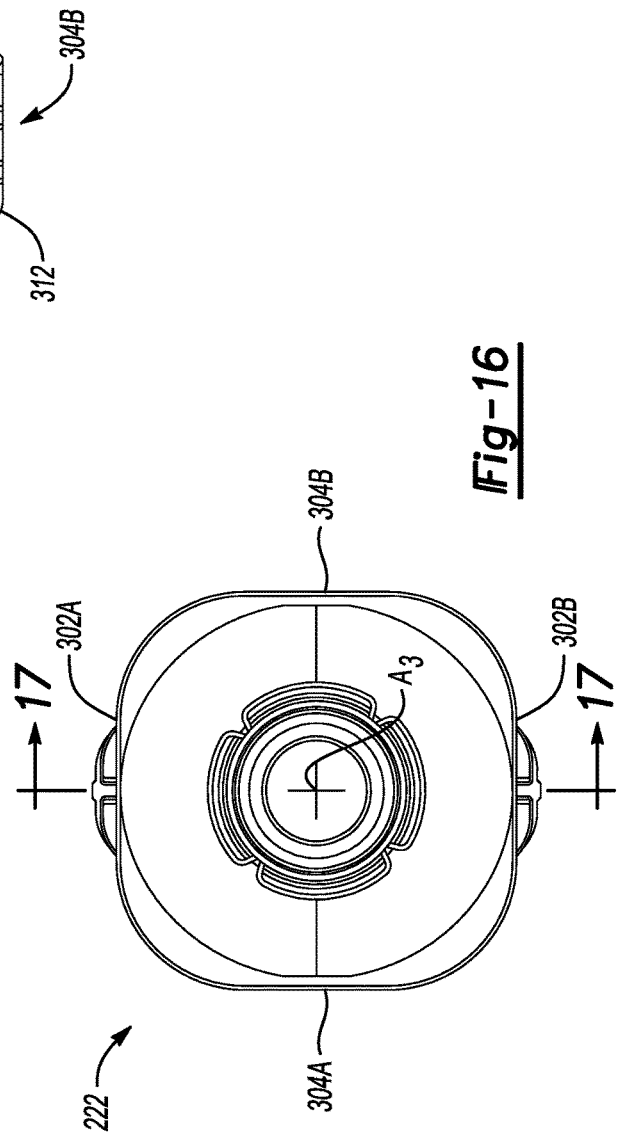

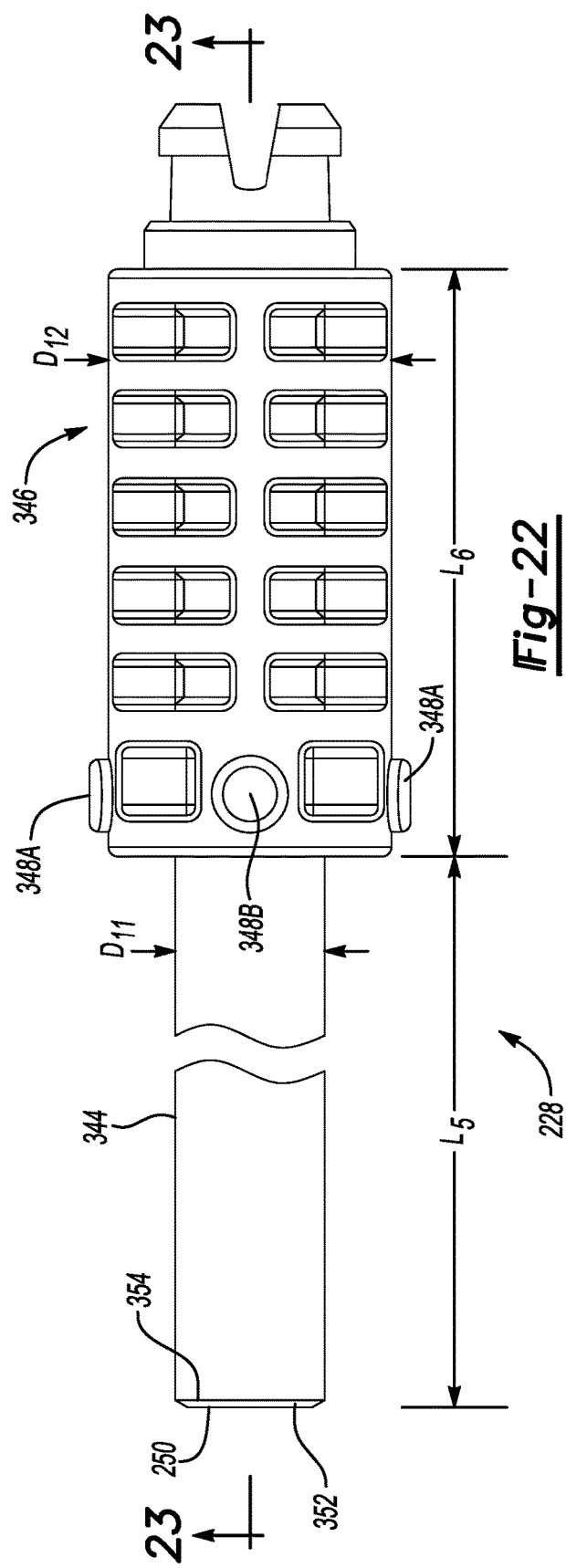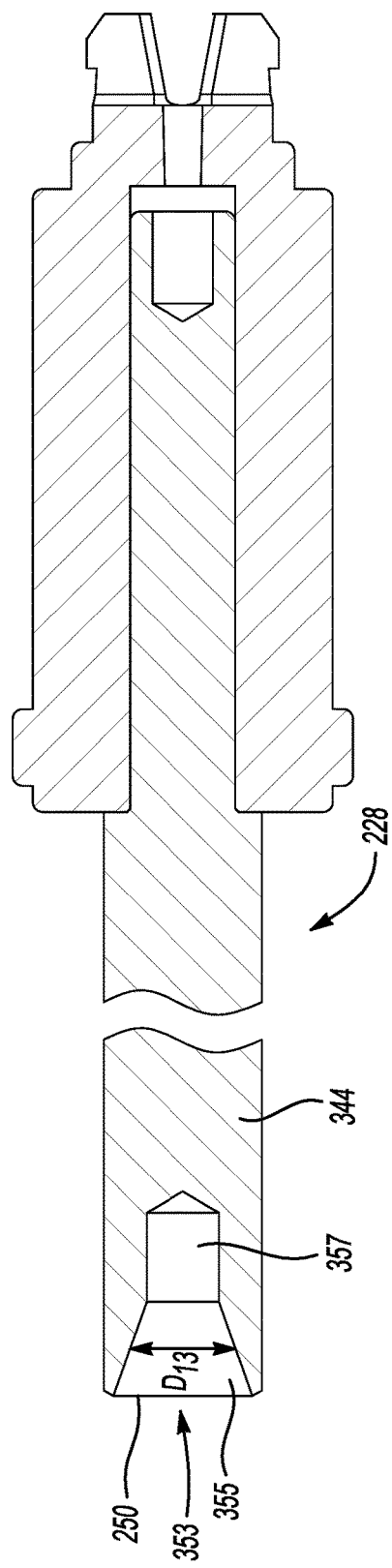

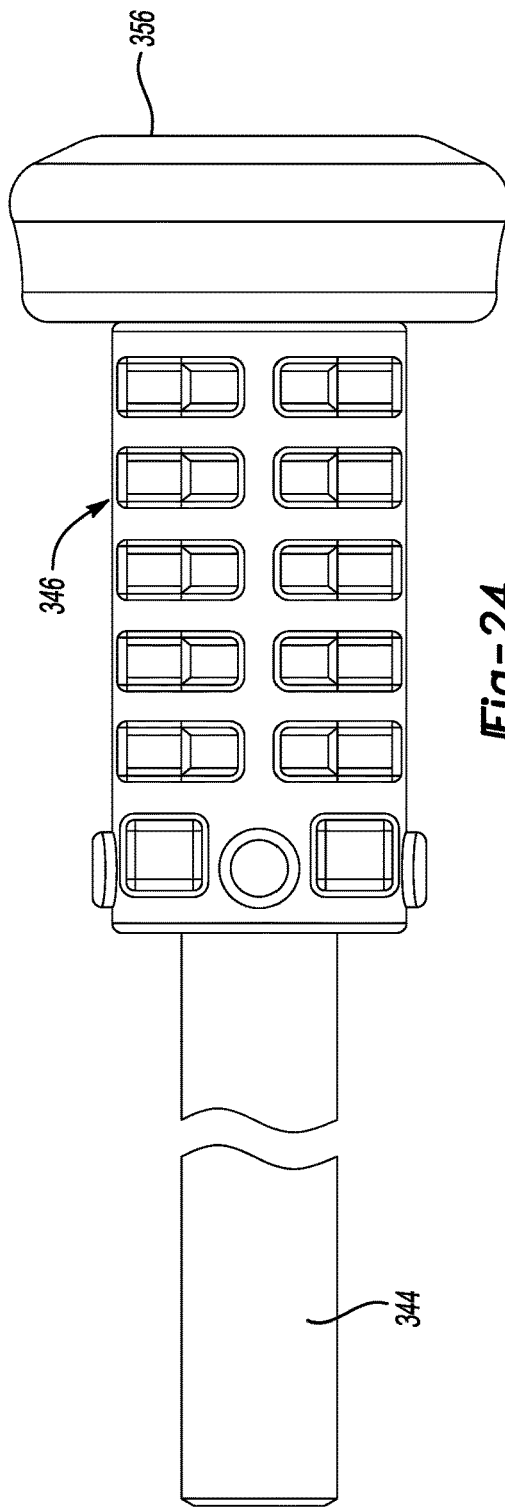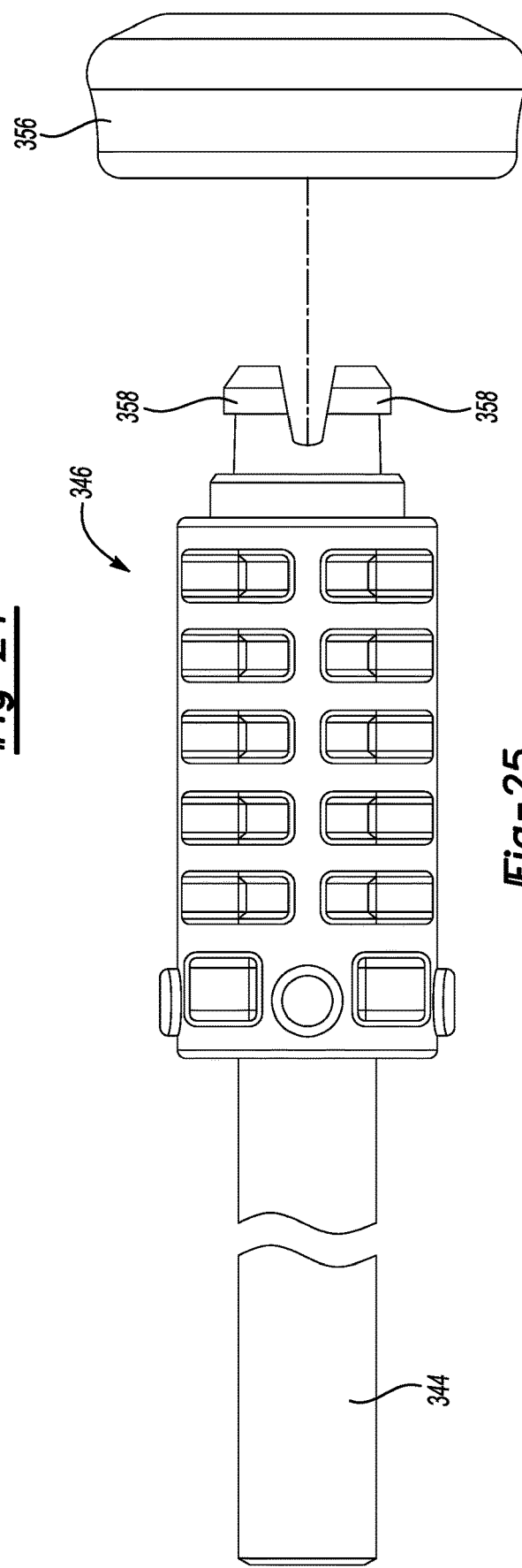

SURGICAL DEVICE CONFIGURED TO STRIP AND CUT TENDON

BACKGROUND

Tendons are commonly harvested for use in orthopedic procedures. In particular, tendons may be autografts harvested from a patient's hamstring tendon, quadriceps tendon, or other areas of the body. The harvested tendons may be used in ligament reconstruction surgeries, e.g., anterior cruciate ligament (ACL), posterior cruciate ligament (PCL), and ulna collateral ligament (UCL) reconstruction surgeries.

SUMMARY

This disclosure relates to a surgical device configured to both strip and cut a tendon. A harvested tendon can be used in various orthopedic procedures, such as ACL, PCL, and UCL reconstructions.

A surgical device according to an exemplary aspect of the present disclosure includes, inter alia, a shaft and an insert adjacent a distal end of the shaft. The insert provides a stripping tube. The stripping tube includes a window permitting a portion of a tendon to enter the insert. Further, the insert includes a cutout proximal of the window and configured such that the portion of the tendon exits the insert by extending through the cutout. An inner diameter of the stripping tube is circular in cross-section, and the stripping tube is centered about a central axis of the shaft. Further, the stripping tube is disposed about the central axis such that the stripping tube provides a continuous hoop about the central axis. An outer diameter of the stripping tube is tapered adjacent a distal edge of the stripping tube such that the outer diameter of the stripping tube gradually reduces toward the distal edge of the stripping tube. The surgical device also includes a cutter moveable distally to sever the tendon such that the portion of the tendon extending through the cutout is separated from a remainder of the tendon by pinching the portion of the tendon between a distal edge of the cutter and a proximal edge of the stripping tube. An outer diameter of the cutter is tapered adjacent the distal edge such that the outer diameter of the cutter gradually reduces toward the distal edge of the cutter. Further, the cutter includes a recess adjacent the distal edge of the cutter and defined by an inner diameter, which is tapered such that the inner diameter defining the recess gradually reduces from the distal edge of the cutter moving proximally.

A surgical device according to another exemplary aspect of the present disclosure includes, inter alia, a shaft and an insert adjacent a distal end of the shaft. The insert provides a stripping tube, which includes a window permitting a portion of a tendon to enter the insert. The insert also includes a cutout proximal of the window and configured such that the portion of the tendon exits the insert by extending through the cutout. An inner diameter of the stripping tube is circular in cross-section, and the stripping tube is centered about a central axis of the shaft. Further, an outer diameter of the stripping tube is tapered adjacent a distal edge of the stripping tube such that the outer diameter of the stripping tube gradually reduces toward the distal edge of the stripping tube. The surgical device further includes a cutter moveable distally to sever the tendon such that the portion of the tendon extending through the cutout is separated from a remainder of the tendon by pinching the portion of the tendon between a distal edge of the cutter and a proximal edge of the stripping tube.

A surgical device according to still another exemplary aspect of the present disclosure includes, inter alia, a shaft and an insert adjacent a distal end of the shaft. The insert provides a stripping tube, which includes a window permitting a portion of a tendon to enter the insert. The insert also includes a cutout proximal of the window and configured such that the portion of the tendon exits the insert by extending through the cutout. An inner diameter of the stripping tube is circular in cross-section, and the stripping tube provides a continuous hoop about a central axis of the shaft. The surgical device further includes a cutter moveable distally to sever the tendon such that the portion of the tendon extending through the cutout is separated from a remainder of the tendon by pinching the portion of the tendon between a distal edge of the cutter and a proximal edge of the stripping tube. An outer diameter of the cutter is tapered adjacent the distal edge such that the outer diameter of the cutter gradually reduces toward the distal edge of the cutter. Further, the cutter includes a recess adjacent the distal edge of the cutter and defined by an inner diameter, which is tapered such that the inner diameter defining the recess gradually reduces from the distal edge of the cutter moving proximally.

BRIEF DESCRIPTION OF THE DRAWINGS

In FIG. 7, a lock assembly is engaged.

In FIG. 8, the lock assembly is disengaged.

In FIG. 9, the stripping tube is in contact with a tendon and the cutter is in a resting position.

In FIG. 10, the cutter has advanced to an intermediate position distal of the resting position.

FIG. 11 is a side view of the surgical device of FIG. 1 with a portion of the handle removed for ease of reference. In FIG. 11, the cutter has advanced distally to a fully deployed position and severed a portion of the tendon.

FIG. 12 is a partial top view of a second example surgical device.

FIG. 15 is a top view of the handle and the shaft of the surgical device of FIG. 13.

FIG. 16 is an end view of the handle of the surgical device of FIG. 13.

FIG. 22 is a side view of a rod and a guide of the surgical device of FIG. 13.

FIG. 23 is a cross-sectional view taken along line 23-23 in FIG. 22.

FIG. 24 is a side view of the rod and the guide of FIG. 22 with a cap attached adjacent an end of the guide.

FIG. 25 is a side view of the rod and the guide of FIG. 22 with the cap detached from the guide.

DETAILED DESCRIPTION

Figure 1:
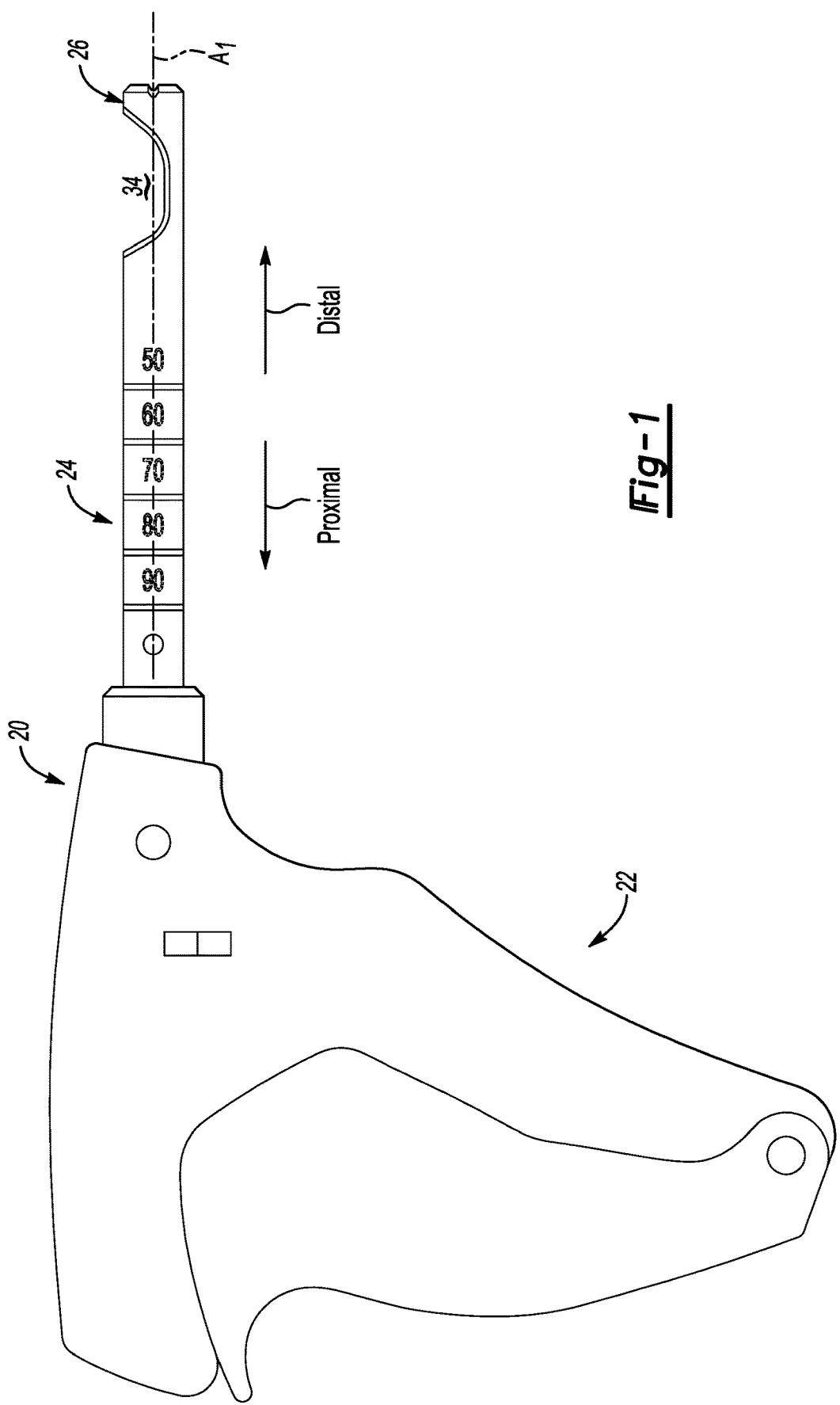
FIG. 1 is a side view of a first example surgical device.

This disclosure relates to a surgical device configured to both strip and cut a tendon. The harvested tendon can be used in various orthopedic procedures, such as ACL, PCL, and UCL reconstructions.

A surgical device according to an exemplary aspect of the present disclosure includes, inter alia, a shaft and an insert adjacent a distal end of the shaft. The insert provides a stripping tube. The stripping tube includes a window permitting a portion of a tendon to enter the insert. Further, the insert includes a cutout proximal of the window and configured such that the portion of the tendon exits the insert by extending through the cutout. An inner diameter of the stripping tube is circular in cross-section, and the stripping tube is centered about a central axis of the shaft. Further, the stripping tube is disposed about the central axis such that the stripping tube provides a continuous hoop about the central axis. An outer diameter of the stripping tube is tapered adjacent a distal edge of the stripping tube such that the outer diameter of the stripping tube gradually reduces toward the distal edge of the stripping tube. The surgical device also includes a cutter moveable distally to sever the tendon such that the portion of the tendon extending through the cutout is separated from a remainder of the tendon by pinching the portion of the tendon between a distal edge of the cutter and a proximal edge of the stripping tube. An outer diameter of the cutter is tapered adjacent the distal edge such that the outer diameter of the cutter gradually reduces toward the distal edge of the cutter. Further, the cutter includes a recess adjacent the distal edge of the cutter and defined by an inner diameter, which is tapered such that the inner diameter defining the recess gradually reduces from the distal edge of the cutter moving proximally.

A surgical device according to another exemplary aspect of the present disclosure includes, inter alia, a shaft and an insert adjacent a distal end of the shaft. The insert provides a stripping tube, which includes a window permitting a portion of a tendon to enter the insert. The insert also includes a cutout proximal of the window and configured such that the portion of the tendon exits the insert by extending through the cutout. An inner diameter of the stripping tube is circular in cross-section, and the stripping tube is centered about a central axis of the shaft. Further, an outer diameter of the stripping tube is tapered adjacent a distal edge of the stripping tube such that the outer diameter of the stripping tube gradually reduces toward the distal edge of the stripping tube. The surgical device further includes a cutter moveable distally to sever the tendon such that the portion of the tendon extending through the cutout is separated from a remainder of the tendon by pinching the portion of the tendon between a distal edge of the cutter and a proximal edge of the stripping tube.

A surgical device according to still another exemplary aspect of the present disclosure includes, inter alia, a shaft and an insert adjacent a distal end of the shaft. The insert provides a stripping tube, which includes a window permitting a portion of a tendon to enter the insert. The insert also includes a cutout proximal of the window and configured such that the portion of the tendon exits the insert by extending through the cutout. An inner diameter of the stripping tube is circular in cross-section, and the stripping tube provides a continuous hoop about a central axis of the shaft. The surgical device further includes a cutter moveable distally to sever the tendon such that the portion of the tendon extending through the cutout is separated from a remainder of the tendon by pinching the portion of the tendon between a distal edge of the cutter and a proximal edge of the stripping tube. An outer diameter of the cutter is tapered adjacent the distal edge such that the outer diameter of the cutter gradually reduces toward the distal edge of the cutter. Further, the cutter includes a recess adjacent the distal edge of the cutter and defined by an inner diameter, which is tapered such that the inner diameter defining the recess gradually reduces from the distal edge of the cutter moving proximally.

In a further embodiment, the cutter is centered about the central axis.

In a further embodiment, the distal edge of the stripping tube comprises a plurality of serrations.

In a further embodiment, an outer diameter of the stripping tube is tapered adjacent a proximal edge of the stripping tube such that the outer diameter of the stripping tube gradually reduces toward the proximal edge of the stripping tube.

In a further embodiment, the shaft projects from a handle, the insert is attached adjacent a distal end of the shaft, the shaft, the insert, and the handle together define a through bore extending along the central axis from a proximal end of the handle to the distal edge of the insert, and the cutter is moveable within the through bore.

In a further embodiment, the through bore exhibits a variable diameter along the central axis.

In a further embodiment, the cutter is provided by a rod, the rod is connected to a guide, the guide includes a projection, the handle includes a helical slot receiving the projection, and the projection and helical slot interact such that movement of the rod and guide along the central axis results in rotation of the rod and guide about the central axis.

In a further embodiment, the projection is one of a plurality of projections spaced-apart from one another about an outer surface of the guide, the helical slot is one of a plurality of helical slots, and each helical slot receives a corresponding one of the projections.

In a further embodiment, a cap is attached to the guide adjacent a proximal end of the guide, the cap is located proximal to the handle, and the cap is configured to rotate relative to the guide.

In a further embodiment, an outer contour of an end section of the handle is substantially square in cross-section with rounded corners.

In a further embodiment, an outer diameter of the insert is configured to prevent rotation and axial movement of the insert relative to the shaft.

FIG. 1 illustrates an example surgical device 20. The surgical device 20 includes a handle 22 and a shaft 24 projecting distally from the handle 22. The "distal" and "proximal" directions are labeled across the various figures for purposes of explanation only. In this example, the shaft 24 includes a stripping tube 26 adjacent to a distal end thereof. The stripping tube 26 is configured to strip tendon. The surgical device 20 includes a cutter 28 (FIG. 2) moveable distally toward the stripping tube 26 to sever tendon. The detail of the surgical device 20, including the stripping tube 26 and cutter 28, will be described below.

Figure 3:
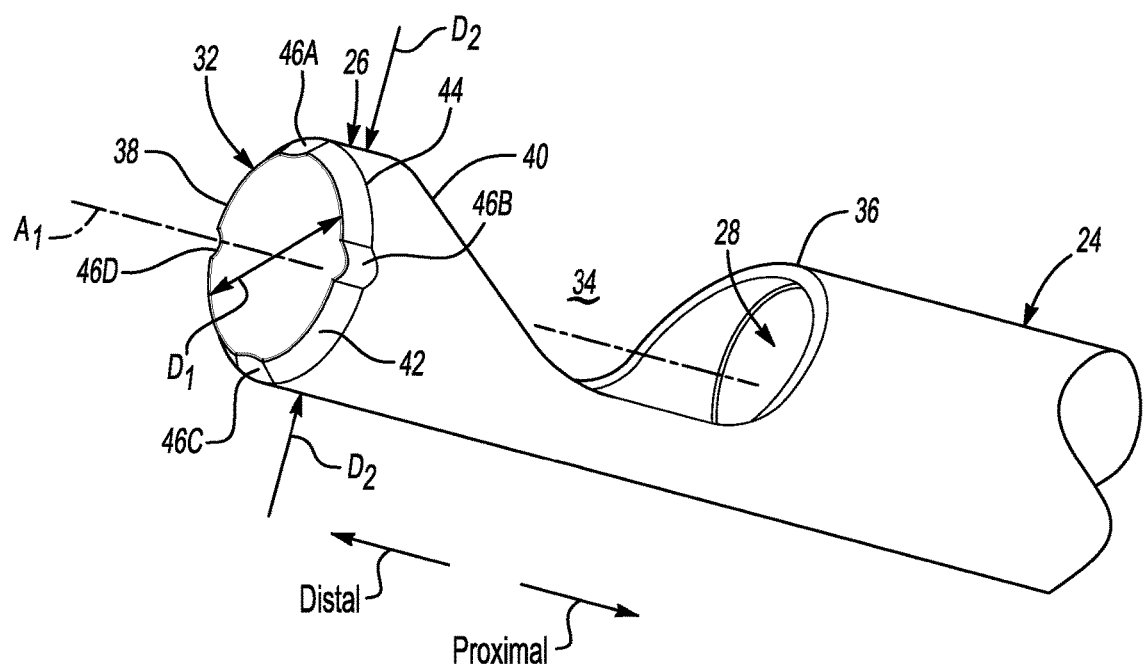
FIG. 3 is a partial side-perspective view of the surgical device of FIG. 1, and in particular illustrates the detail of a stripping tube.

With reference to FIG. 3, the shaft 24 comprises a substantially cylindrical body, which may be made of a metallic material. While the shaft 24 is substantially cylindrical in this example, the shaft 24 could exhibit different cross-sectional shapes, including being substantially square or rectangular. The shaft 24 extends along an axis $A_1$, which is the central longitudinal axis of the shaft 24. Adjacent to a distal end 32 of the shaft 24, the shaft 24 includes a cutout 34 in a superior surface 36 (i.e., an upper surface) thereof. The cutout 34 allows a tendon to pass therethrough and defines the structure of the stripping tube 26, as will be discussed below.

The stripping tube 26 is a portion of the shaft 24 and extends completely around the axis $A_1$ in this example. The stripping tube 26 includes a distal edge 38 and a proximal edge 40. The distal edge 38 is the coextensive with the distal end 32 of the shaft 24, in this example. The proximal edge 40 of the stripping tube 26 is defined by a distal boundary of the cutout 34. An inner diameter $D_1$ of the stripping tube 26 intersects the axis $A_1$, such that the inner diameter $D_1$ of the stripping tube 26 is substantially circular in cross-section. In this way, the stripping tube 26 includes a window allowing a portion of a tendon to pass therethrough.

The distal edge 38 of the stripping tube 26 is configured to strip a portion of a tendon from adjacent tissue. In this example, the stripping tube 26 is tapered adjacent to the distal edge 38. In particular, an outer diameter $D_2$ of the stripping tube 26 gradually reduces in diameter throughout a tapered section 42. The tapered section 42 extends axially from the distal edge 38 to a location 44 proximal of the distal edge 38. The tapered section 42, in one example, is arranged such that the distal edge 38 is a sharp edge, meaning the distal edge 38 is tapered to a sharp point. In other examples, the distal edge 38 may be rounded or blunt while still capable of stripping a tendon. Further, in this example, tapered section 42 extends around the entirety of the axis $A_1$, but in other examples the tapered section 42 may extend only partially about the axis $A_1$.

In order to increase the ability of the stripping tube 26 to strip tendon, the stripping tube 26 may include one or more serrations adjacent to the distal edge 38. In this example, the stripping tube 26 includes four serrations 46A-46D. The serrations 46A-46D are equally spaced-apart from one another about the axis $A_1$. In this example, the serrations 46A-46D are notches extending proximally of the distal edge 38. This disclosure is not limited to any particular number or arrangement of serrations.

The substantially circular inner diameter $D_1$ allows one to harvest tendons that are substantially cylindrical, which allows one to harvest a properly-sized, cylindrical tendon without needing to approximate a cylindrical shape using a number of rectilinear cuts. In this regard, the stripping tube 26 exhibits the substantially circular inner diameter $D_1$ along the entire length of the stripping tube 26. Further, the inner diameter $D_1$ may be selected to correspond to a desired diameter of the harvested tendon. As examples, the inner diameter $D_1$ may be 7 mm, 10 mm, or 12 mm, although this disclosure is not limited to these particular dimensions. A surgeon may have a number of surgical devices 20 at their disposal, each of which has a stripping tube 26 of a different inner diameter $D_1$. The surgeon may select a surgical device 20 having an appropriately sized inner diameter $D_1$ for use in a particular procedure. In this way, the stripping tube 26 also acts as a sizing tube.

The cutter 28 is moveable distally toward the stripping tube 26 in order to sever, or cut, tendon. In this example, the cutter 28 comprises a substantially cylindrical body that is disposed about the axis $A_1$ and arranged within the shaft 24. The cutter 28 may be made of a metallic material. Like the shaft 24, the cutter 28 may also exhibit a different cross-sectional shape, such as being substantially square or rectangular in cross-section. This disclosure is not limited to a substantially cylindrical shaft 24 and cutter 28. The cutter 28 has an outer diameter $D_3$, which is substantially the same as the inner diameter $D_1$ of the stripping tube 26. In this example, the outer diameter $D_3$ is slightly less than the inner diameter $D_1$ to allow the cutter 28 to move relative to the shaft 24.

Figure 2:
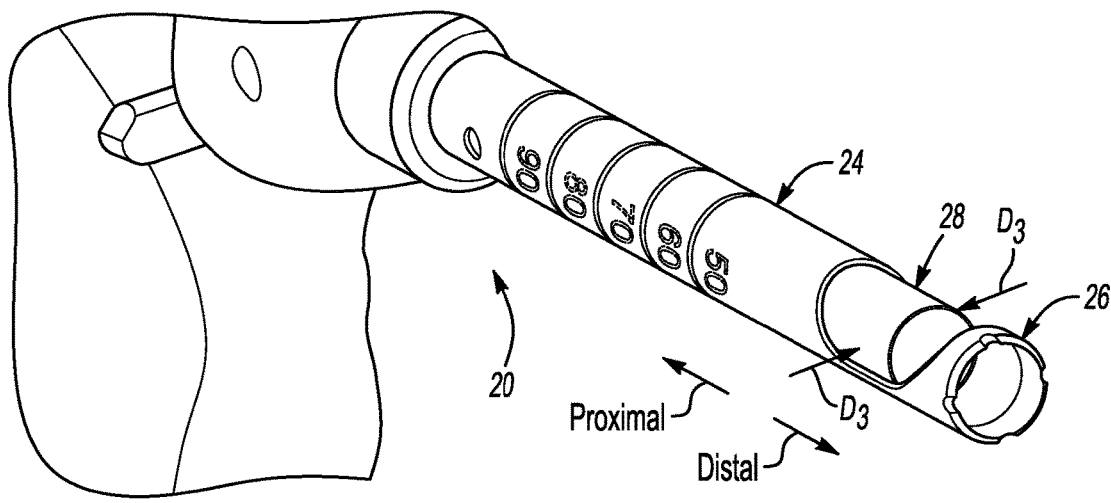
FIG. 2 is a partial perspective view of the surgical device of FIG. 1, and in particular illustrates a cutter in an intermediate position between a resting position and a fully deployed position.
Figure 4:
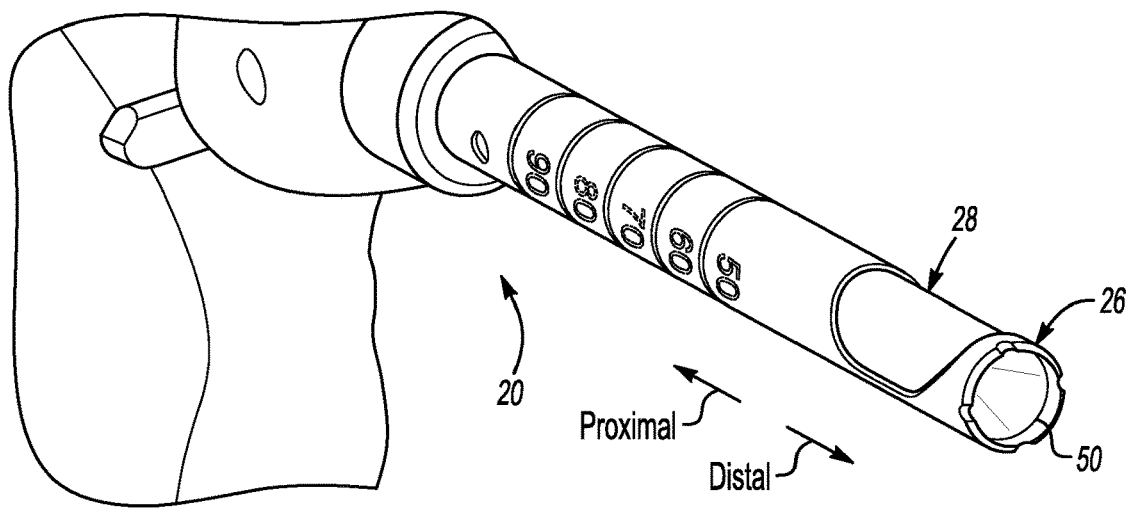
FIG. 4 is a partial perspective view of the surgical device of FIG. 1, and in particular illustrates the cutter in a fully deployed position.
Figure 5:
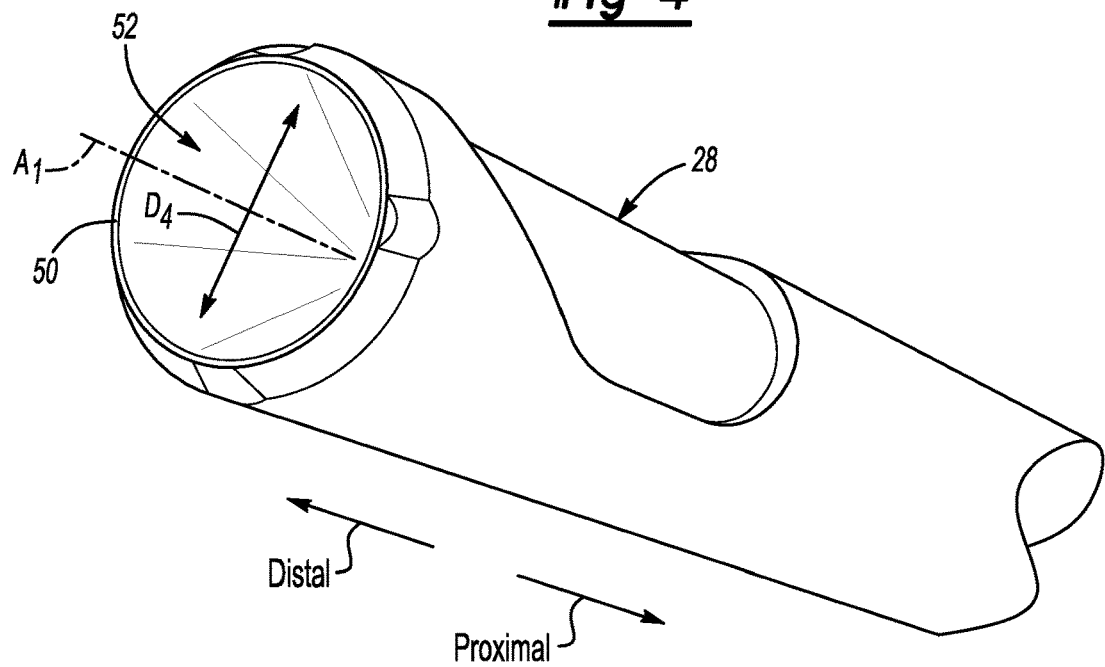
FIG. 5 is a partial side-perspective view of the surgical device of FIG. 1, and in particular illustrates the detail of the cutter.

The cutter 28 is selectively moveable within the shaft 24 under the force of a trigger and one or more biasing elements, which will be discussed below. The cutter 28 is moveable from a neutral, resting position to a fully deployed position. The resting position is shown in FIGS. 1 and 3, in which the entirety of the cutter is proximal of the cutout 34. FIGS. 4 and 5 illustrate the cutter 28 in the fully deployed position, in which the cutter 28 has moved distally relative to the resting position, and a distal edge 50 of the cutter 28 is distal of the cutout 34. For reference, FIG. 2 illustrates the cutter 28 in an intermediate position between the resting position and the fully deployed positions.

To increase the ability of the cutter 28 to sever a tendon, the cutter 28 is tapered adjacent to its distal edge 50. In this example, the outer diameter $D_3$ of the cutter 28 is substantially constant along the length of the cutter 28, and the cutter 28 includes a recess 52 (FIG. 5) adjacent to the distal edge 50. The recess 52 is tapered as it extends proximally from the distal edge 50. In particular, the recess 52 is defined by an inner diameter $D_4$, which gradually reduces from the distal edge 50 moving proximally. Thus, the recess 52 is substantially frustoconical in shape, although this disclosure is not limited to frustoconically-shaped recesses, and extends to other shapes such as rounded or squared recesses. The recess 52 may be such the distal edge 50 is a sharp edge, rounded edge, or blunt. In either instance, the recess 52 is such that the distal edge 50 effectively cuts tendon. While not shown in this embodiment, the cutter 28 may include one or more serrations, similar to the serrations 46A-46D, adjacent to the distal edge 50.

Figure 6:
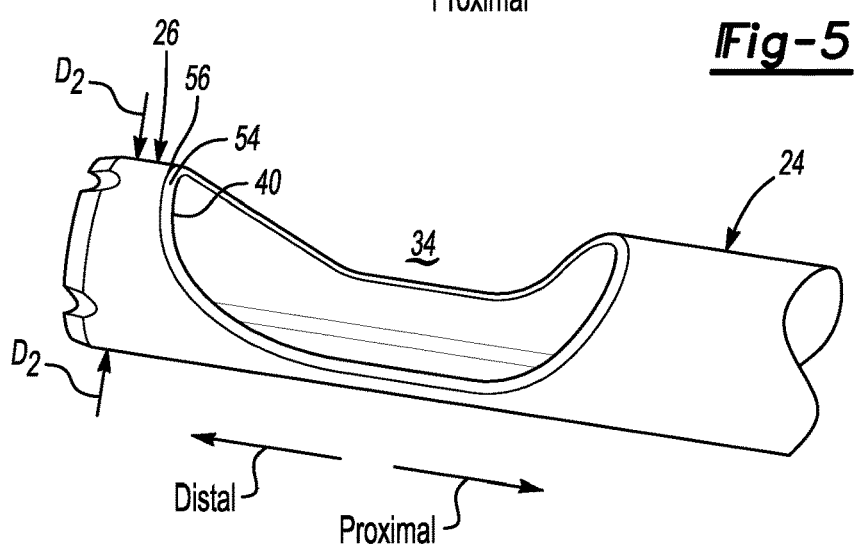
FIG. 6 is a partial top-perspective view of the surgical device of FIG. 1, and in particular illustrates the detail of the stripping tube and an adjacent cutout.

As a tendon is being stripped, the removed portion of the tendon exits the shaft 24 through the cutout 34. In order to sever the removed portion of the tendon, a user moves the cutter 28 distally toward the proximal edge 40 of the stripping tube 26. The tendon is severed by being pinched, and cut, between the proximal edge 40 of the stripping tube 26 and the distal edge 50 of the cutter 28. In one example, the proximal edge 40 of the stripping tube 26 is tapered to increase the ease of cutting tendon. As shown in FIG. 6, the stripping tube 26 may include a tapered section 54 beginning at a location 56 distal of the proximal edge 40. The outer diameter $D_2$ of the stripping tube 26 gradually reduces throughout the tapered section 54 moving proximally from location 56 to the proximal edge 40. The proximal edge 40 may be a sharp edge, rounded edge, or blunt. While in the illustrated embodiment both the proximal edge 40 and the distal edge 50 are tapered, in other examples only one of the proximal edge 40 and the distal edge 50 is tapered.

Figure 7:
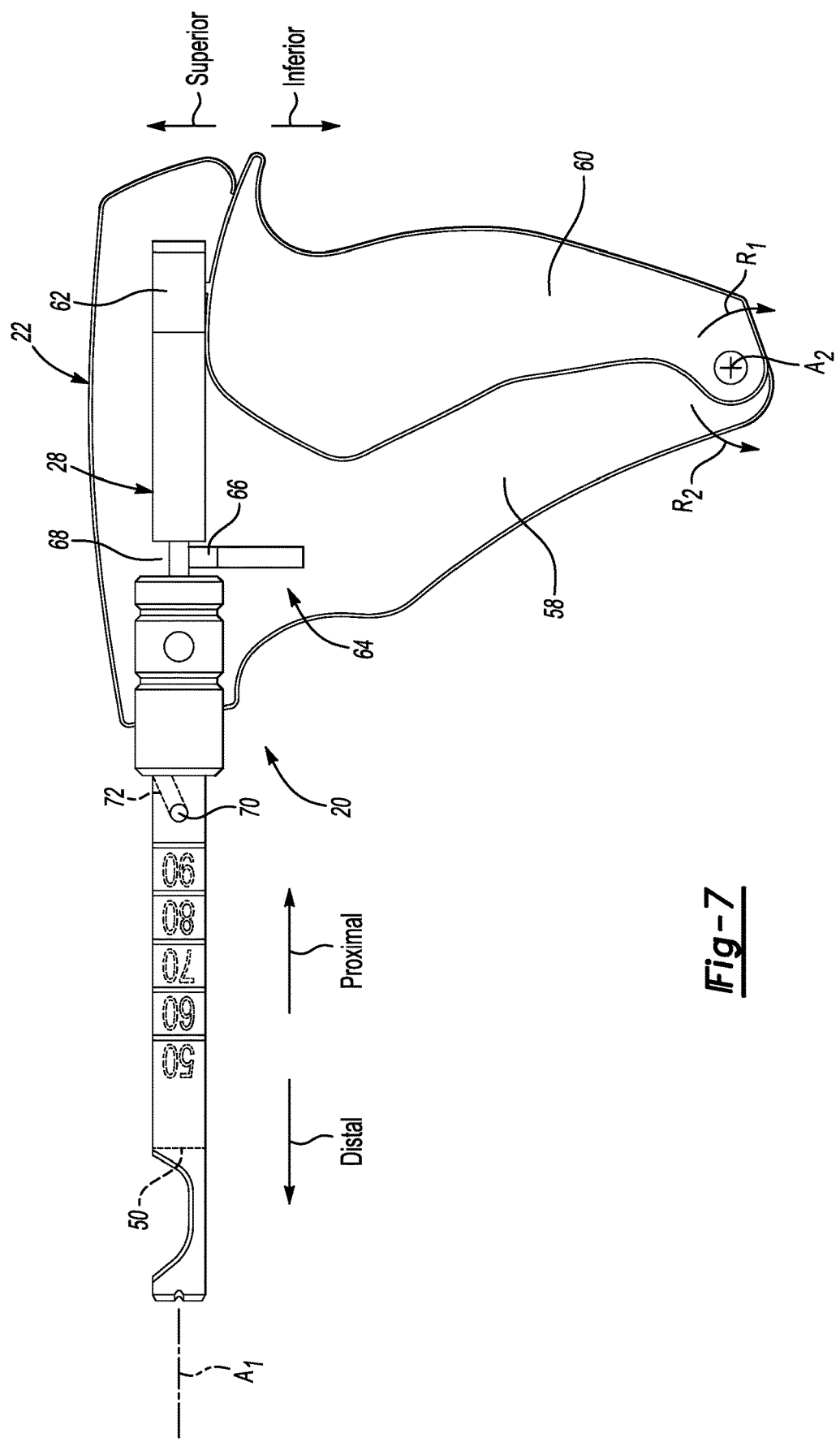
FIG. 7 is a side view of the surgical device of FIG. 1 with a portion of a handle removed for ease of reference.

With reference to FIG. 7, an example arrangement of the handle 22 will now be described. In particular, an example arrangement configured to effect movement of the cutter 28 relative to the stripping tube 26 will be described. This disclosure is not limited to surgical devices including the particular arrangement of FIG. 7.

In FIG. 7, an exterior cover of the handle 22 is partially removed for ease of reference. The handle 22 includes a grip 58 and a trigger 60 rotatable relative to the grip about an axis $A_2$ adjacent to an inferior portion (i.e., bottom) of the grip 58. The "inferior" and "superior" directions are labeled in FIG. 7 for purposes of explanation only. The axis $A_2$ is normal to the axis $A_1$ in this example. The trigger 60 is proximal to the grip 58 and the handle 22 is arranged such that the trigger 60 rests between a user's thumb and index finger when a user grasps the grip 58.

The trigger 60 is mechanically coupled to the cutter 28 by way of a projection 62 projecting in the superior direction (i.e., an upper direction) from the remainder of the trigger 60. In this way, rotation of the trigger 60 about axis $A_2$ is translated into axial movement of the cutter 28 along the axis $A_1$.

In FIG. 7, the cutter 28 is in the resting position, in which the distal edge 50 of the cutter 28 is proximal of the cutout 34. One or more biasing elements may bias the cutter 28 and/or the trigger 60 toward the resting position. For example, the handle 22 may include one or more biasing elements urging the cutter 28 in the proximal direction, and the handle may include one or more biasing elements urging the trigger 60 to rotate in a first direction $R_1$ about the axis $A_2$, which in this example is a clockwise direction.

In order to move the cutter 28 distally toward the fully deployed position, a user applies a force to the trigger 60 to overcome the bias of the cutter 28 and/or the trigger 60 toward the resting position. To activate the trigger 60, a user applies a distal force onto the trigger 60, causing the trigger 60 to rotate in a second direction $R_2$ opposite the first direction $R_1$, which ultimately causes distal movement of the cutter 28. Deploying the cutter 28 is intuitive for the user because applying a distal force onto the trigger 60 is translated into distal movement of the cutter 28.

Figure 8:
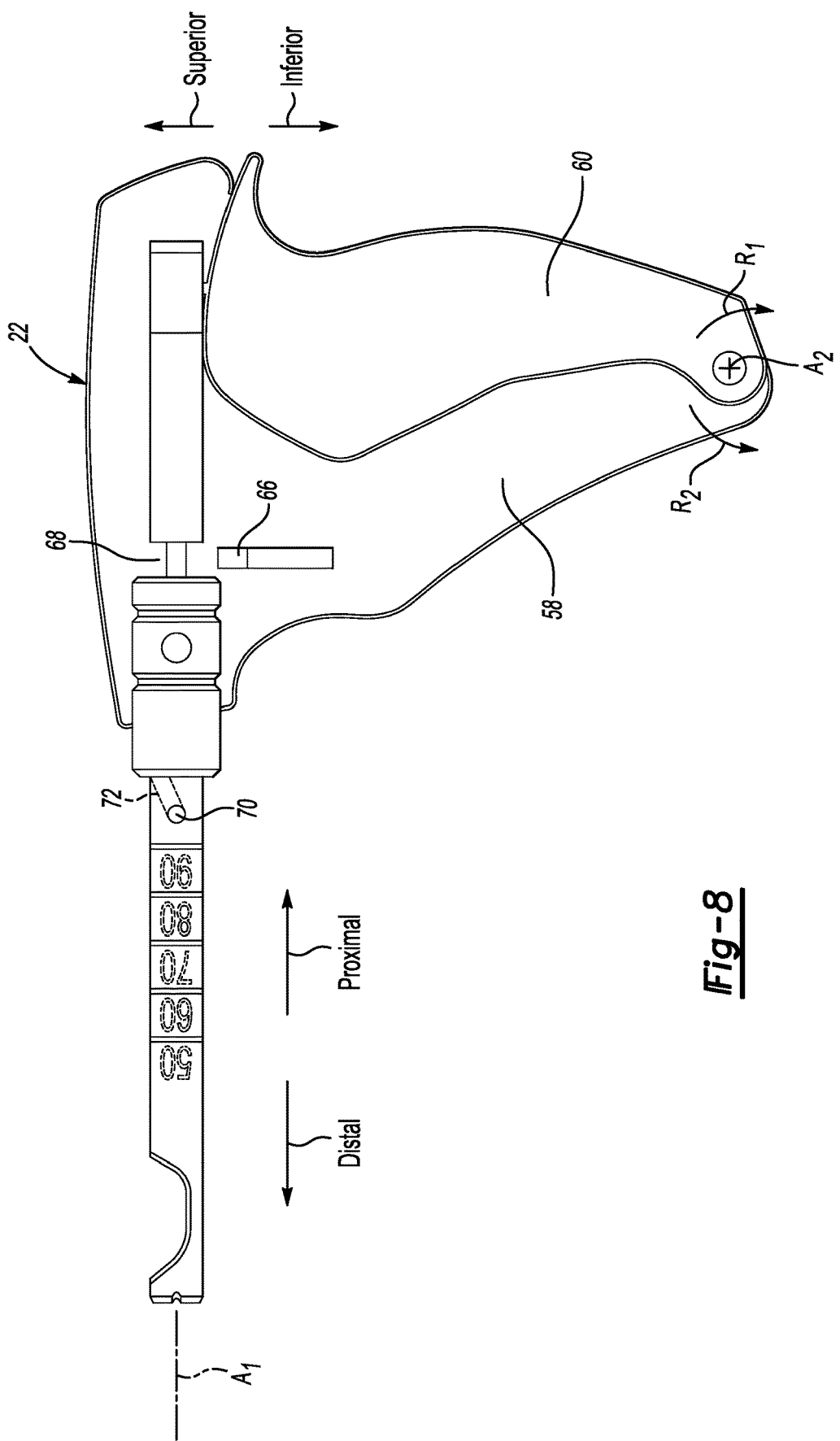
FIG. 8 is a side view of the surgical device of FIG. 1 with a portion of a handle removed for ease of reference.

In an aspect of this disclosure, unintended deployment of the cutter 28 is prevented by way of a lock assembly 64. The lock assembly 64 includes a tab 66 moveable in the superior and inferior directions in and out of a slot 68 formed in the cutter 28. In FIG. 7, the lock assembly 64 is engaged, meaning the tab 66 is in the slot 68, which prevents axial movement of the cutter 28 and holds the cutter 28 in the resting position. In FIG. 8, the tab 66 has moved in the inferior direction relative to FIG. 7 to disengage the lock assembly 64, such as by a user applying a downward force to the tab 66. In FIG. 8, the tab 66 is not within the slot 68, and thus the tab 66 does not prevent axial movement of the cutter 28. This disclosure is not limited to surgical devices with lock assemblies.

With reference back to FIG. 7, in another aspect of this disclosure the surgical device 20 is arranged such that the cutter 28 rotates about the axis $A_1$ as it moves along the axis $A_1$. Rotating the cutter 28 relative to the stripping tube 26 may increase the ease of severing tendon. To rotate the cutter 28 in an embodiment, the surgical device 20 includes a pin 70 supported by the shaft 24 and projecting in a direction normal to the axis $A_1$. The cutter 28 includes at least one helical slot 72 formed therein. The helical slot 72 is shown in phantom in FIG. 7, and extends helically along the axis $A_1$. The pin 70 is arranged such that it projects into the helical slot 72. The interaction between the pin 70 and the helical slot 72 causes the cutter 28 to rotate about the axis $A_1$ as it moves axially along the axis $A_1$. The cutter 28 is not required to rotate in all examples, but, as mentioned, rotation may increase the ease of cutting. Further, it should be understood that this disclosure extends to configurations where the cutter 28 is fixed and the stripping tube 26 is configured to rotate about the axis $A_1$ as the stripping tube 26 moves axially relative to the cutter 28. While only one pin 70 and helical slot 72 are shown in FIG. 7, it should be understood that the shaft 24 and the cutter 28 may include additional pins and helical slots, respectively.

Figure 9:
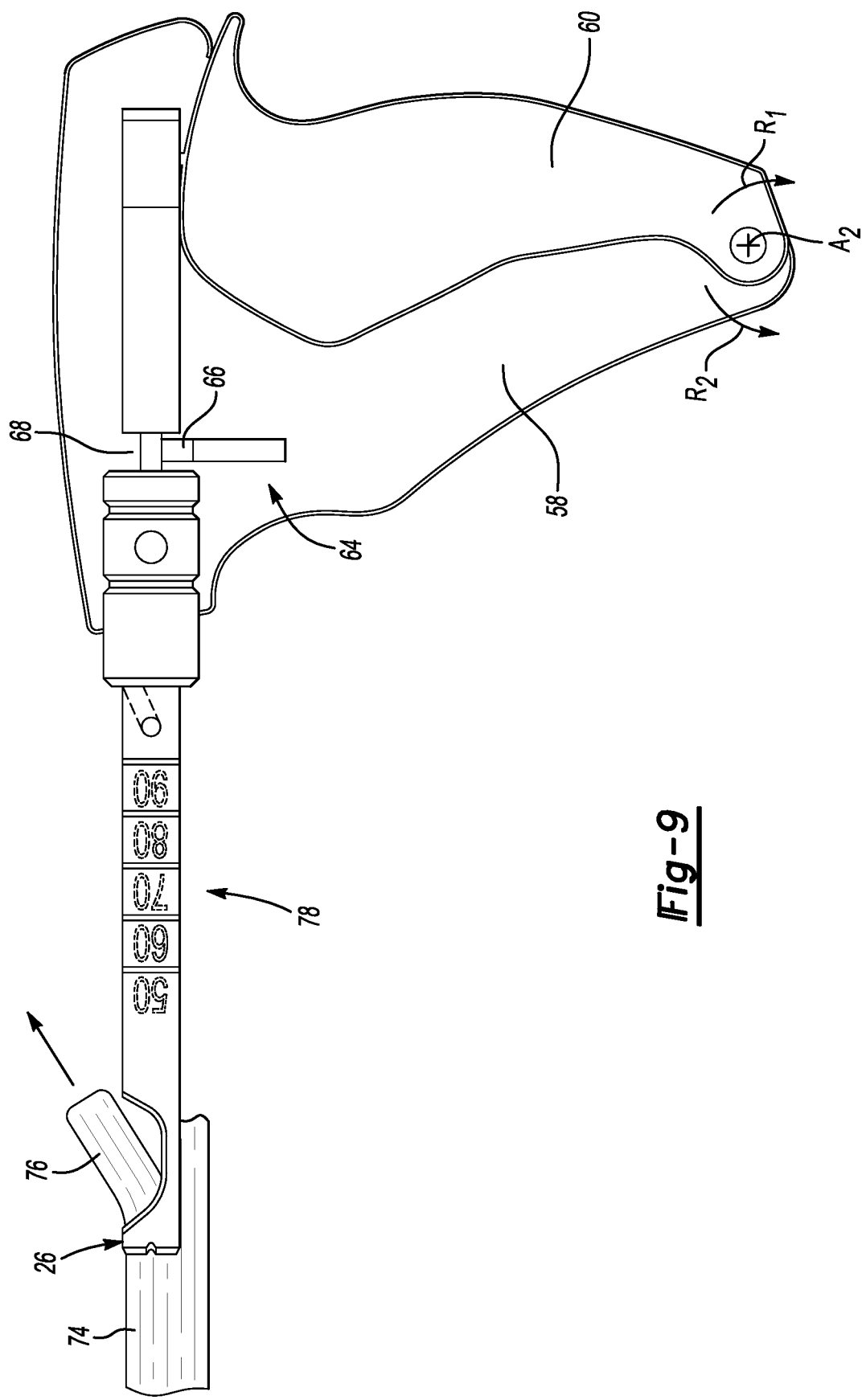
FIG. 9 is a side view of the surgical device of FIG. 1 with a portion of the handle removed for ease of reference.

An example method of use will now be described with reference to FIGS. 9-11. In FIG. 9, the surgical device 20 is in contact with a tendon 74 and begins to strip the tendon. When stripping tendon 74 in this example, the cutter 28 is in the resting position, and the lock assembly 64 is engaged. Thereby, the tab 66 prevents unwanted movement of the cutter 28, which may otherwise sever a tendon prematurely.

In FIG. 9, a user strips the tendon 74 by bringing the distal edge 38 of the stripping tube 26 into contact with the tendon 74 and advancing the surgical device 20 distally along the tendon 74. A portion of the tendon 74 enters the stripping tube 26 and becomes partially separated from the remainder of the tendon 74. The partially separated portion of the tendon is labeled with reference numeral 76. The portion 76 is substantially cylindrical in cross-section by virtue of the substantially circular cross-section of the stripping tube 26.

The tendon 74 may be a quadriceps tendon in one example. This disclosure is not limited to any particular type of tendon, however. Further, this disclosure may be used with other types of soft tissue and is not limited to use with tendons.

In the example method, a user continues advancing the surgical device 20 distally until the portion 76 is of a desired graft length. The user may measure the portion 76 using markings 78 on the exterior of the shaft 24. The markings 78 correspond to a distance proximal of the cutout 34, and may be in millimeters spaced-apart by units of 10 (e.g., 50, 60, 70, 80, 90). The markings 78 are shown in phantom in the figures to avoid confusion with the other reference numerals used in the figures and discussed herein. The shaft 24 need not include markings in all examples.

Figure 10:
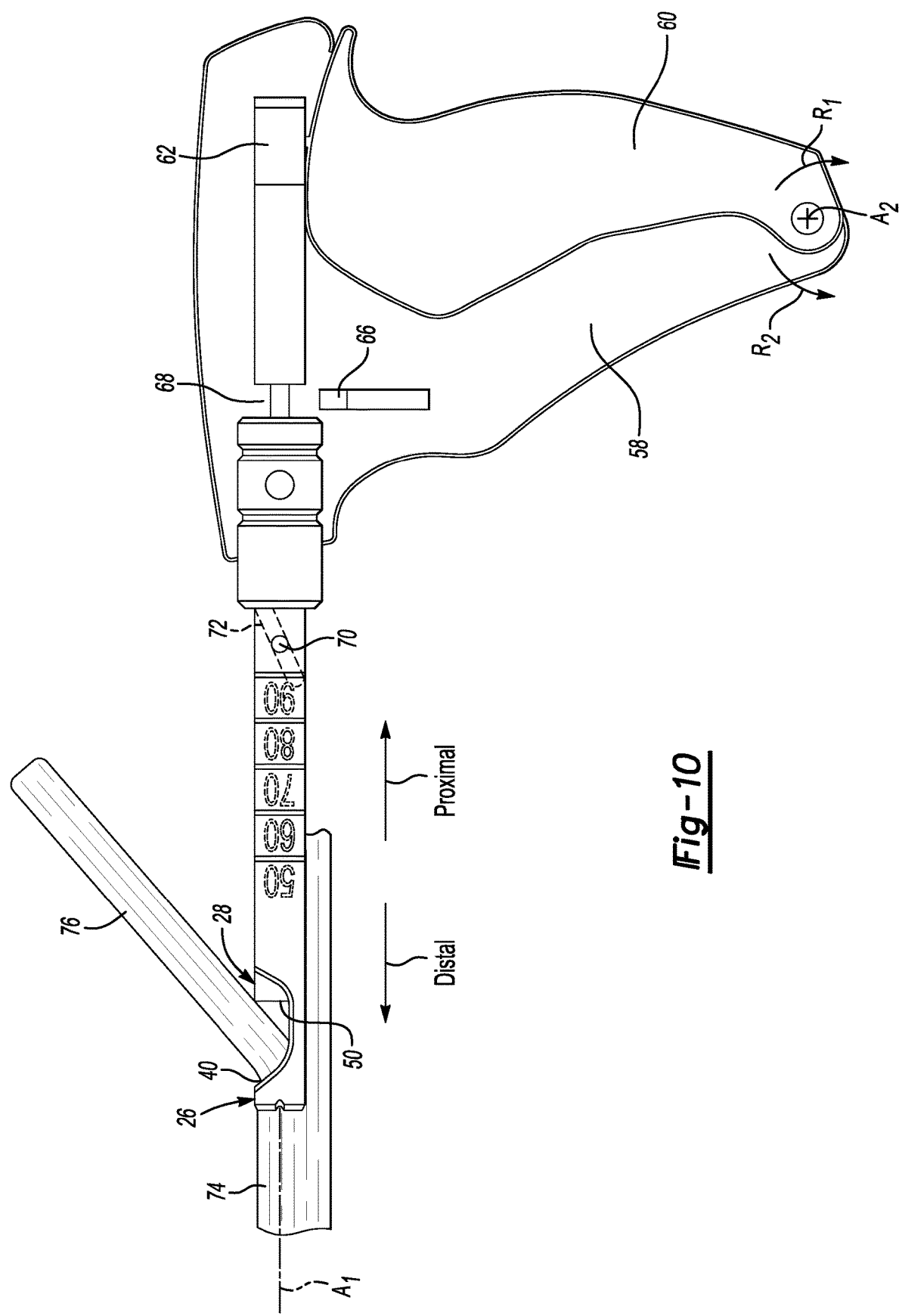
FIG. 10 is a side view of the surgical device of FIG. 1 with a portion of the handle removed for ease of reference.

In FIG. 10, the user has advanced the surgical device 20 distally to a point where the portion 76 of the tendon 74 will provide an adequate graft length. Thus, the user has disengaged the lock assembly 64 by moving the tab 66 in the inferior direction and has begun advancing the cutter 28 distally. The user has activated the trigger 60 by squeezing the grip 58 and trigger 60 together, thereby rotating the trigger 60 in the direction $R_2$ about the axis $A_2$. Such rotation results in distal movement of the cutter 28 along the axis $A_1$ by virtue of projection 62 being mechanically coupled to the cutter 28. The axial movement of the cutter 28 also results in rotational movement of the cutter 28 about the axis $A_1$ by virtue of the arrangement of the pin 70 and the helical slot 72.

Continued squeezing causes additional distal movement of the cutter 28, which in turn causes the portion 76 of the tendon 74 to become pinched between the distal edge 50 of the cutter 28 and the proximal edge 40 of the stripping tube 26. Ultimately, the portion 76 is completely severed from the remainder of the tendon 74, as shown in FIG. 11, in which the cutter 28 is in the fully deployed position. Among other benefits, the surgical device 20 is intuitive and allows one to harvest tendon using fewer instruments than prior techniques.

FIG. 12 is a top view of a portion of another example surgical device 120. To the extent not otherwise described or shown, the surgical device 120 corresponds to the surgical device 20, with like parts preappended with a "1."

Unlike the surgical device 20, in which the cutter 28 is disposed circumferentially within the shaft 24, the surgical device 120 is arranged such that the cutter 128 is disposed circumferentially outward of the shaft 124. The cutter 128 may be moveable between a resting position and a fully deployed position in substantially the same way as described relative to FIGS. 7-11. The cutter 128 may rotate as it moves axially, as in the previous embodiment. Alternatively, the cutter 128 need not rotate.

In an additional embodiment, the stripping tube 126 is substantially similar to that of the stripping tube 26, with the exception of the proximal edge 140. In FIG. 12, the proximal edge 140 of the stripping tube 126 is not tapered. Rather, the proximal edge 140 is blunt and includes a rounded projection 180 projecting proximally of a superior surface 182 of the stripping tube 126. In a variation of this embodiment, the proximal edge 140 may be tapered, in generally the same way as the proximal edge 40. In still another variation, the proximal edge 140 does not include the rounded projection 180.

The distal edge 150 of the cutter 128 is also arranged differently than in the previous embodiment. In FIG. 12, the outer diameter $D_3$ of the cutter 128 includes a tapered section 184 extending from the distal edge 150 to a location 186 proximal of the distal edge 150. The outer diameter $D_3$ gradually reduces in thickness moving distally throughout the tapered section 184. The cutter 128 also includes at least one serration 188 adjacent to the distal edge 150. In FIG. 12, the cutter 128 includes only one serration 188, which is a notch formed in the distal edge 150 in this example. The serration 188 is symmetrical about a plane passing through the axis $A_1$ and bisecting the surgical device 120. The serration 188 is aligned with the projection 180 such that a common plane bisects both the projection 180 and the serration 188. The projection 180 and the serration 188 cooperate with one another to provide effective cutting of a tendon. While only one serration 188 is shown in FIG. 12, the cutter 128 may include additional serrations. Alternatively, the cutter 128 may not include any serrations.

Another example surgical device 220 will now be described. To the extent not otherwise described or shown, the surgical device 220 corresponds to the surgical device 20, with like parts preappended with a "2."

Figure 13:
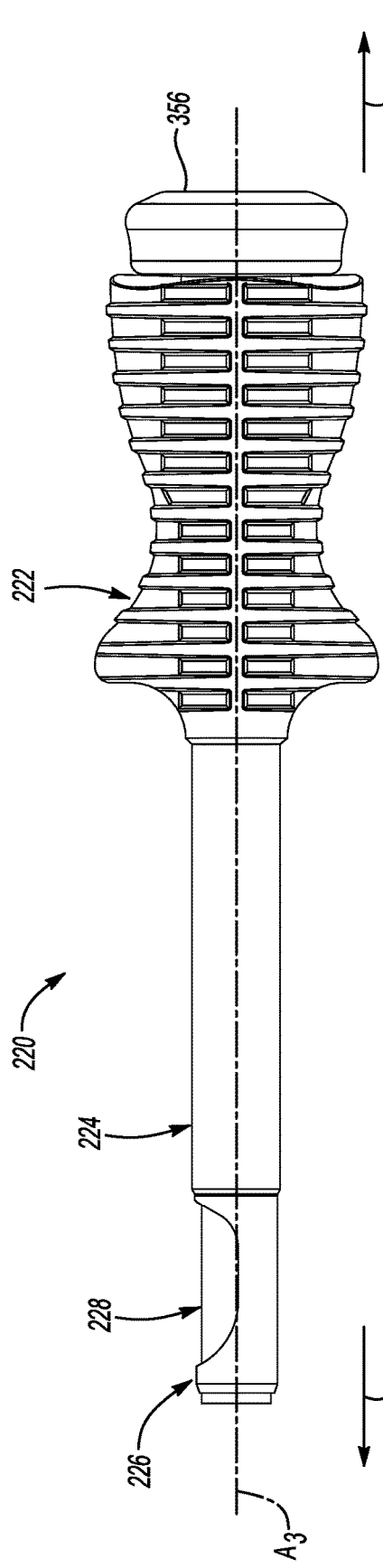
FIG. 13 is a side view of a third example surgical device.

FIG. 13 is a side view of the example surgical device 220. The surgical device 220 includes a handle 222 and a shaft 224 projecting distally from the handle 222. Further, a stripping tube 226 is adjacent a distal end of the shaft 224. The stripping tube 226 is configured to strip tendon. The surgical device 220 includes a cutter 228 moveable distally toward the stripping tube 226 to sever tendon.

With reference to FIGS. 14-17, the handle 222 and shaft 224 are integrally formed in this example. The handle 222 and shaft 224 may be made of a metallic material or from another type of material, such as polycarbonate, as examples. The handle 222 exhibits an outer contour configured to be grasped by a hand of a user, such as surgeon.

When viewed from an end, as in FIG. 16, the outer contour of the handle 222 is substantially square with rounded corners. The corners connect a first set of opposed surfaces 302A, 302B and a second set of opposed surfaces 304A, 304B. The first set of opposed surfaces 302A, 302B exhibit the same contour, reflected about an axis $A_3$, which is the central longitudinal axis of the surgical device 220. The second set of opposed surfaces 304A, 304B also exhibit the same contour, reflected about the axis $A_3$. Further, the contour of the second set of opposed surfaces 304A, 304B is different than the first set of opposed surfaces 302A, 302B, which provides a user with more than one option for gripping the handle 222. The user may find certain hand positions more comfortable depending on personal preference and/or on the relative position of the user and the patient, for example. Further, the substantially square outer contour allows for optimal torque transmission.

Figure 14:
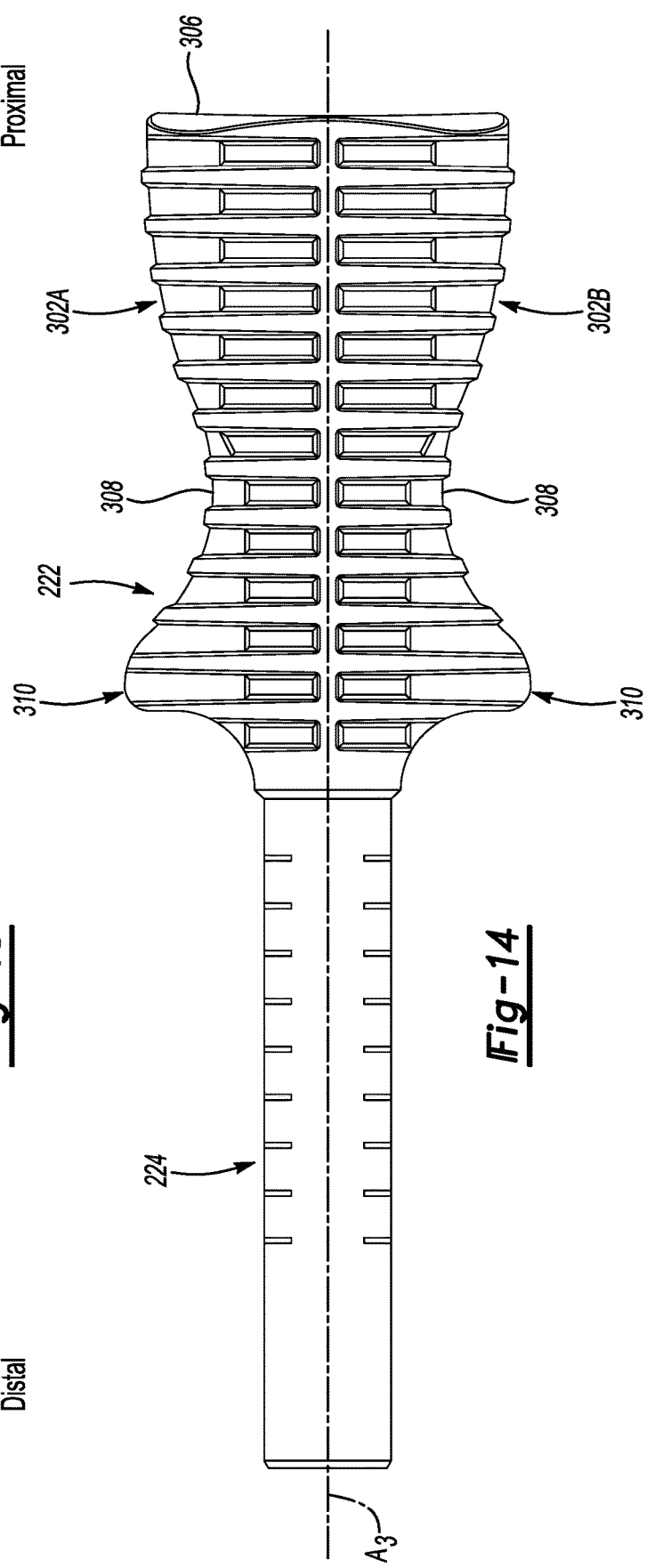
FIG. 14 is a side view of a handle and a shaft of the surgical device of FIG. 13.

With reference to FIG. 14, additional detail of first set of opposed surfaces 302A, 302B will now be described. Beginning adjacent a proximal end 306 of the handle 222 and moving distally, the surfaces 302A, 302B gradually taper toward the axis $A_3$ such that the handle 222 reduces in diameter to an axial location 308. At location 308, surfaces 302A, 302B are closest to the axis $A_3$. Distal of location 308, the surfaces 302A, 302B gradually diverge from the axis $A_3$ to form a flared portion 310, at which point the handle 222 exhibits its largest diameter, in this example. In particular, at the flared portion 310, the surfaces 302A, 302B are slightly further from the axis $A_3$ than at locations adjacent the proximal end 306 of the handle 222. Distal of the flared portion 310, the handle 222 converges toward axis $A_3$ and the surfaces 302A, 302B blend into the shaft 224.

With reference to FIG. 15, the second set of opposed surfaces 304A, 304B exhibit a substantially constant diameter beginning adjacent the proximal end 306 of the handle 222 and moving distally to an axial location 312. The location 312 is proximal of the location 308. Distal of the location 312, the surfaces 304A, 304B gradually taper toward the axis $A_3$ and eventually blend into the shaft 224. The surfaces 304A, 304B do not diverge from the axis $A_3$ moving distally along the length of the surfaces 304A, 304B, and in particular the surfaces 304A, 304B do not exhibit a flared portion similar to the flared portion 310, in this example.

Figure 17:
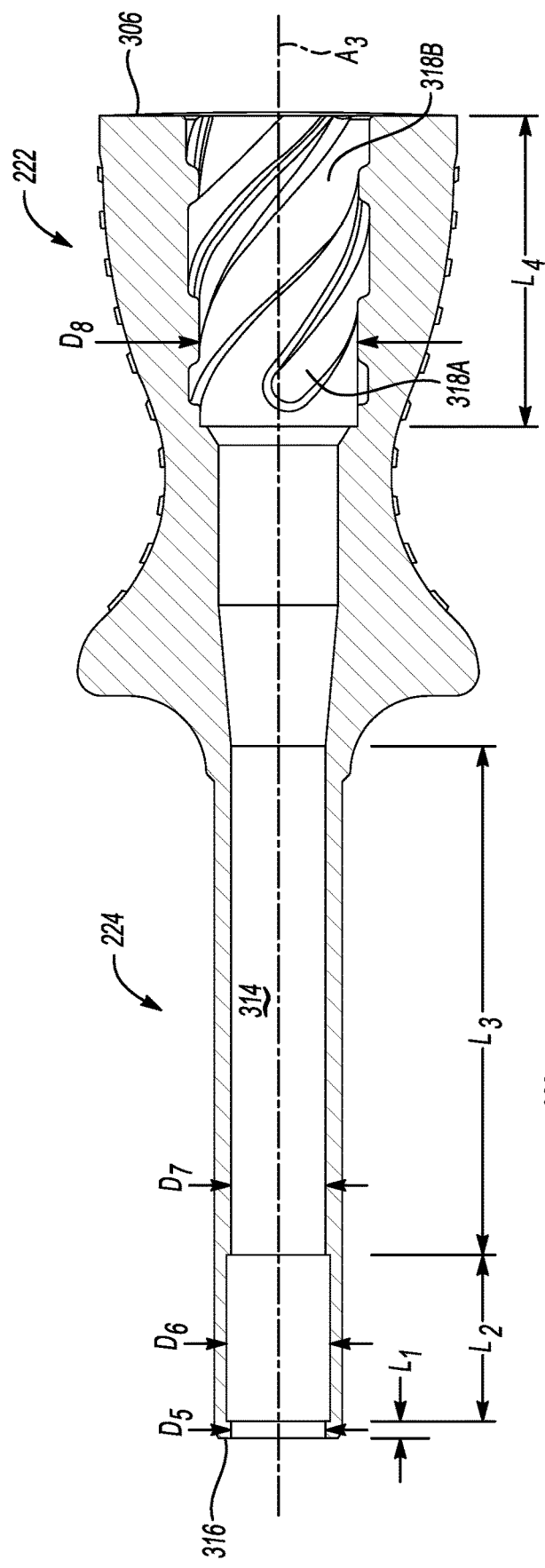
FIG. 17 is a cross-sectional view taken along line 17-17 from FIG. 16.
Figure 18:
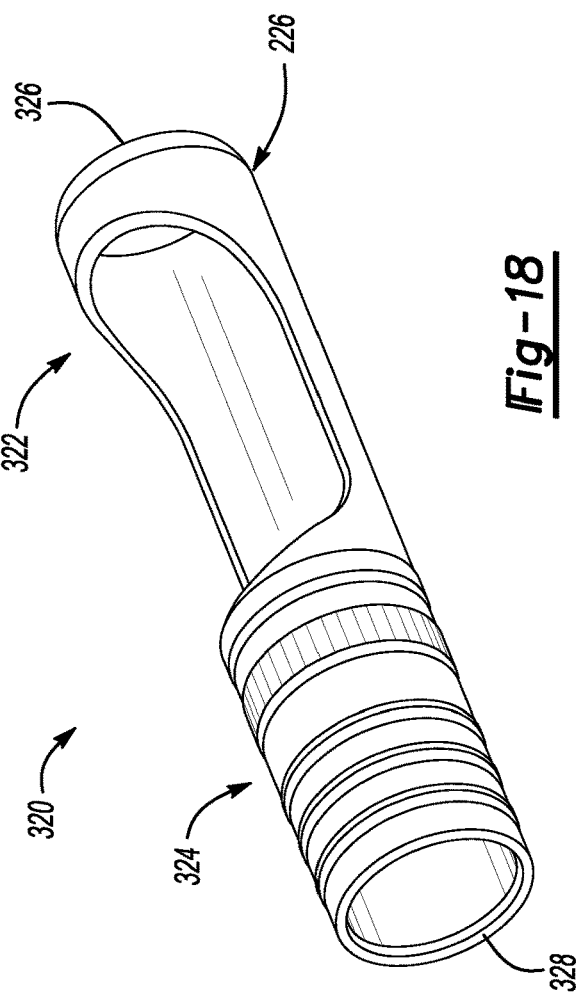
FIG. 18 is a rear-perspective view of a stripping tube insert of the surgical device of FIG. 13.

With reference to FIG. 17, the handle 222 and shaft 224 include a through bore 314 extending along the entirety of the handle 222 and shaft 224. Specifically, the through bore 314 extends from the proximal end 306 of the handle 222 to the distal end 316 of the shaft 224. Adjacent the distal end 316, the through bore 314 is configured to receive and support the stripping tube 226 relative to the shaft 224. The through bore 314 is also configured to facilitate movement of the cutter 228 within the through bore 314. The through bore 314 is centered around the axis $A_3$ and exhibits a variable diameter, which is a dimension passing through the axis $A_3$, along the length of the through bore 314. The through bore 314 exhibits a circular cross-section along most of its length.

Beginning at the distal end 316 and moving proximally, the through bore 314 exhibits a diameter $D_5$ along a length $L_1$. The inner surface of the diameter $D_5$ may include features, such as projections, configured to interface with corresponding features on an exterior surface of the stripping tube 226 to prevent rotation and/or axial movement of the stripping tube 226. Exemplary features will be discussed below relative to the stripping tube insert 320, which provides the stripping tube 226 in this example. Proximal of the length $L_1$, the through bore widens to a diameter $D_6$ greater than diameter $D_5$ along a length $L_2$. Along the length $L_2$, the through bore 314 may also include features configured to interface with features on the exterior surface of the stripping tube 226 to prevent relative rotation and/or axial movement between the stripping tube 226 and the shaft 224. Along length $L_3$, which is proximal to length $L_2$, the through bore narrows and exhibits a diameter $D_7$ less than the diameter $D_6$.

Beginning at the proximal end 306 of the handle 222 and moving distally, within the handle 222 the through bore 314 exhibits a diameter $D_8$ over a length $L_4$. Within the length $L_4$, the through bore 314 also includes two helical slots 318A, 318B in this example. The helical slots 318A, 318B extend radially outward of the diameter $D_8$ and extend helically along the axis $A_3$. The helical slots 318A, 318B are configured to receive pins associated with the cutter 228 and are arranged such that interaction between the pins and the helical slots 318A, 318B causes the cutter 228 to rotate about the axis $A_3$ as it moves axially along the axis $A_3$. Distal of the length $L_4$, the diameter of the through bore 314 gradually reduces and blends into the diameter $D_7$.

The stripping tube 226 of the surgical device 220 is not integrally formed with the shaft 224 in this example. Rather, the stripping tube 226 is provided by a separately-formed structure, which is referred to herein as a stripping tube insert 320, and is shown in FIGS. 18-21. The stripping tube insert 320 is press-fit into the distal end 316 of the shaft 224 or connected to the shaft 224 in another manner. The stripping tube insert 320 includes a distal section 322 providing the stripping tube 226 and configured to strip and cut soft tissue. The stripping tube insert 320 also includes a proximal section 324 configured to fit within the through bore 314 and hold the stripping tube insert 320 to the shaft 224 by resisting rotation and axial movement of the stripping tube insert 320 relative to the shaft 224.

Figure 19:
FIG. 19 is an end view of the stripping tube insert.

With reference to FIG. 19, the stripping tube insert 320 exhibits a constant interior diameter $D_9$ along the entirety of the length of the stripping tube insert 320, from its distal end 326 to its proximal end 328. In this manner, the stripping tube insert 320 defines a through bore along an entirety of its length. When the stripping tube insert 320 is supported relative to the shaft 224 as in FIG. 13, the interior diameter $D_9$ is centered around the axis $A_3$ and essentially continues the through bore 314 such that the surgical device 220 exhibits a through bore extending from the proximal end 306 of the handle to the distal end 326 of the stripping tube insert 320. The interior of the stripping tube insert 320 is substantially circular in cross-section along the entirety of its length in this example.

Figure 20:
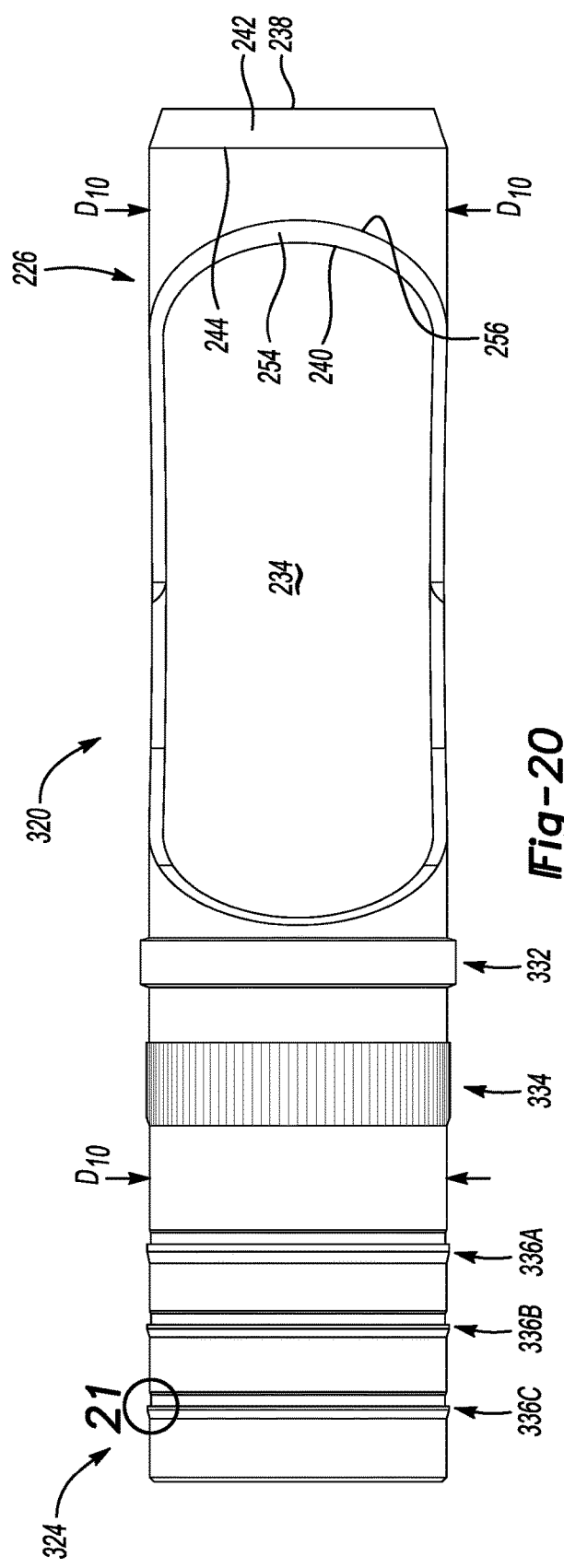
FIG. 20 is a top view of the stripping tube insert.
Figure 21:
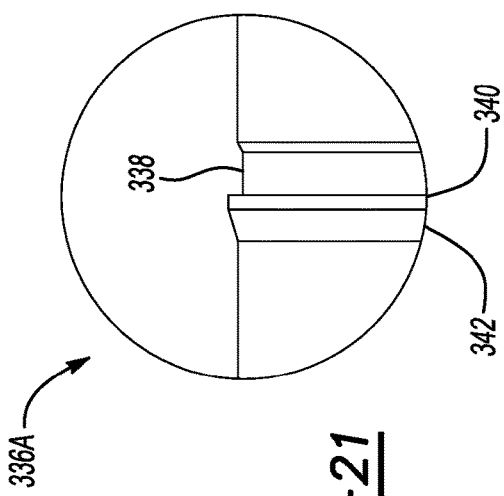
FIG. 21 is a close-up view of a portion of the stripping tube insert.

With reference to FIG. 20, the stripping tube 226 is configured substantially the same as the stripping tube 26. The stripping tube 226 includes a distal edge 238, which is coextensive with the distal end 326 (FIG. 18), and a proximal edge 240. The proximal edge 240 of the stripping tube 226 is defined by a distal boundary of a cutout 234 in a superior surface of the stripping tube insert 320. The distal edge 238 of the stripping tube 226 defines a window 330 (FIG. 19) allowing a portion of a tendon to pass therethrough.

The distal edge 238 of the stripping tube 226 is configured to strip a portion of a tendon from adjacent tissue. The stripped portion of tendon enters the window 330, passes through the interior of the stripping tube 226 and ultimately exits the surgical device 220 via the cutout 234.

In this example, to facilitate cutting, the stripping tube 226 is tapered adjacent to the distal edge 238. In particular, an outer diameter $D_{10}$ of the stripping tube 226 gradually reduces in diameter throughout a tapered section 242. The tapered section 242 extends axially from the distal edge 238 to a location 244 proximal of the distal edge 238. The tapered section 242, in one example, is arranged such that the distal edge 238 is a sharp edge, meaning the distal edge 238 is tapered to a sharp point. Tapering the distal edge 238 permits effective cutting of a tendon while also protecting against inadvertent cutting of adjacent soft tissues, such as the paratendon. In other examples, the distal edge 238 may be rounded or blunt while still capable of stripping a tendon. Further, in this example, tapered section 242 extends around the entirety of the axis $A_3$. To this end, the stripping tube 226 extends continuously about the axis $A_3$ such that the stripping tube 226 defines a continuous, uninterrupted hoop, as shown in FIG. 19.

The stripping tube 226 also includes a tapered section 254 beginning at a location 256 distal of the proximal edge 240. Specifically, the outer diameter $D_{10}$ of the stripping tube 226 gradually reduces throughout the tapered section 254 moving proximally from location 256 to the proximal edge 240. The proximal edge 240 may be a sharp edge, rounded edge, or blunt. The tapered section 254 facilitates cutting of the stripped portion of tendon as that stripped portion of tendon is pinched between a distal edge of the cutter 228 and the proximal edge 240.

Proximal of the cutout 234, the proximal section 324 of the exterior of the stripping tube insert 320 includes a number of features configured to interface with the shaft 224, and in particular the through bore 314, in order to hold the stripping tube insert 320 relative to the shaft 224. A majority of the proximal section 324 of the stripping tube insert exhibits the diameter $D_{10}$. Moving proximally from the cutout 234, the stripping tube insert 320 includes a raised section 332 having a greater diameter than the diameter $D_{10}$. Proximal of the raised section 332, the stripping tube insert 320 steps back down to the diameter $D_{10}$. Moving proximally, the stripping tube insert 320 includes a plurality of longitudinally-extending projections 334, each of which are circumferentially spaced-apart from one another about the exterior of the stripping tube insert 320. The longitudinally-extending projections 334 are splines in one example and, in that example, may be formed by spline rolling. The longitudinally-extending projections 334 are configured to interface and mate with corresponding features of the through bore 314 to prevent relative rotation of the stripping tube insert 320 and the shaft 224.

Proximal of the longitudinally-extending projections 334, the stripping tube insert 320 includes a plurality of retention features 336A-336C axially spaced-apart from one another and configured to resist axial movement of the stripping tube insert 320 relative to the shaft 224. With specific reference to the retention feature 336A, the retention features 336A-336C are formed by a channel 338 recessed inward of the diameter $D_{10}$, a raised surface 340 immediately proximal of the channel 338 and projecting radially outward of the diameter $D_{10}$, and an inclined surface 342 tapering proximally from the raised surface 340 such that, moving proximally, the inclined surface 342 gradually blends into the diameter $D_{10}$. The channels 338, raised surface 340, and inclined surface 342 extend continuously about the entire outer circumference of the stripping tube insert 320. While a particular arrangement of features configured to resist axial and rotational movement of the stripping tube insert 320 has been shown and described, this disclosure extends to other such arrangements.

The stripping tube insert 320 is press-fit into the through bore 314 by inserting into the through bore 314 adjacent the distal end 316 of the shaft 224. By forming the stripping tube insert 320 as a separate structure from the handle 222 and shaft 224, a user may select a particular stripping tube insert 320 for use in a particular procedure. In particular, a user may have access to a kit having stripping tube inserts exhibiting diameters $D_9$ of different sizes and/or different cross-sectional shapes, and the user may select a particular stripping tube insert from the kit for use in a particular procedure so as to obtain a desired graft size and/or shape.

The cutter 228 will now be described with reference to FIGS. 22 and 23. In general, the cutter 228 is moveable within the through bore 314 to cut a portion of tendon projecting through the cutout 234. In this example, the cutter 228 is provided by a rod 344, which drawn as broken along its length in FIGS. 22-24 for ease of illustrating the rod 344 without showing its full length $L_5$. The rod 344 exhibits a substantially constant exterior diameter $D_{11}$ along its length $L_5$, which extends from a distal edge 250 of the rod 344 to a point at which the rod 344 is attached to a guide 346. As shown in FIG. 23, a portion of the rod 344 may pass into the guide 346. The diameter $D_{11}$ is such that the rod 344 is able to move axially within the through bore 314 and the interior of the striping tube insert 320.

The guide 346 exhibits a diameter $D_{12}$ greater than the diameter $D_{11}$ along a length $L_6$. The diameter $D_{12}$ corresponds to the diameter $D_8$ of the through bore 314. In this example, the guide 346 includes two sets of pins 348A, 348B circumferentially spaced-apart from one another about the guide 346 and sized so as to be received within the helical slots 318A, 318B. The pins 348A, 348B interface with the helical slots 318A, 318B to convert axial movement of the cutter 228 along the axis $A_3$ into rotation of the cutter 228 about the axis $A_3$, which increases the ease of cutting tendon.

The distal edge 250 of the rod 344 is tapered in this example. In particular, the outer diameter $D_{11}$ of the rod 344 gradually reduces throughout the tapered section 352 moving distally from location 354, which is proximal to the distal edge 250, to the distal edge 250. The distal edge 250 may be a sharp edge, rounded edge, or blunt. The tapered section 354 facilitates cutting of the stripped portion of tendon but also reduces undesired cutting of adjacent soft tissues.

The inner diameter of the rod 344 adjacent the distal edge 250 is also tapered. In particular, the rod 344 includes a recess 353 adjacent the distal edge 250. The recess 353 includes a tapered section 355 having a frustoconical shape and having a gradually reducing inner diameter $D_{13}$ as the recess 353 extends proximally from the distal edge 250. In this example, the recess 353 includes a proximal section 357 proximal of the tapered section 355 to facilitate machining of the tapered section 355. The proximal section 357 exhibits a diameter equal to or less than the smallest diameter of the tapered section 355. The tapered section 355 facilitates the cutting of tendon. Together, the tapered sections 354, 355 concentrate cutting forces and increase the ease of cutting tendon.

Proximal of the guide 346, a cap 356 is attached to the guide 346 via a plurality of deflectable tabs 358 on the guide 346, as shown in FIGS. 24 and 25. The cap 356 interfaces with the deflectable tabs 358 such that the deflectable tabs 358 restrict axial movement of the cap 356 but permit rotation of the cap 356 relative to the guide 346. When assembled, the cap 356 is proximal to the handle 222, as shown in FIG. 13.

In order to move the cutter 228, a user may grasp the handle 222 with one hand and the cap 356 with another hand. The user may apply a force to the cap 356 to move the rod 344 and guide 346 axially along the axis $A_3$. As that force is applied, the guide 346 and rod 344 rotate about the axis $A_3$ by virtue of the helical slots 318A, 318B and the pins 348A, 348B. Since the cap 356 is rotatable relative to the rod 344 and guide 346, however, rotation of the rod 344 and guide 346 is not transmitted to the cap 356. Thus, the user is not forced to adjust their grip on the cap 356 when moving the cutter 228. This may be particularly beneficial as the user typically will be wearing latex gloves, which may be prone to tearing if exposed to excess friction.

Various features of the surgical device 220 may be combined with features of the surgical device 20, except where such features are not combinable. As one example, while serrations are not shown on the surgical device 220, the serrations 46A-46D of the surgical device 20 can be incorporated into the surgical device 220. Further, the surgical device 220 can include markings similar to the markings 78.

The surgical device 220 is used to strip tendon in substantially the same manner as the surgical device 20, with a main exception being that instead of a trigger, the cutter 228 moves distally, similar to what is shown in FIGS. 10 and 11, as a user applies force to the cap 356. Another exception includes that the cutter 228, including the rod 344, guide 346, and cap 356, may be detached from the stripping tube insert 320, handle 222, and shaft 224 as tendon is stripped, as in FIG. 9. The cutter 228 may then be inserted into the through bore 314 when cutting is desired. As such, surgical device 220 is effectively a two-part system that prevents inadvertent and/or premature deployment of the cutter 228.

It should be understood that terms such as "distal," "proximal," "superior," "inferior," etc., have been used herein for purposes of explanation, and should not be considered otherwise limiting. Terms such as "generally," "substantially," "about," "slightly," etc., are not intended to be boundary less terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A surgical device, comprising:
   a shaft;
   an insert adjacent a distal end of the shaft, wherein the insert is formed as a separate structure from the shaft, wherein the insert provides a stripping tube, wherein the stripping tube includes a window permitting a portion of a tendon to enter the insert, wherein the insert includes a cutout proximal of the window and configured such that the portion of the tendon exits the insert by extending through the cutout, wherein an inner diameter of the stripping tube is circular in cross-section, wherein the stripping tube is centered about a central axis of the shaft, wherein the stripping tube is disposed about the central axis such that the stripping tube provides a continuous hoop about the central axis, wherein an outer diameter of the stripping tube is tapered adjacent a distal edge of the stripping tube such that the outer diameter of the stripping tube gradually reduces toward the distal edge of the stripping tube, wherein the insert defines a through bore along an entirety of a length of the insert; and a cutter moveable distally to sever the tendon such that the portion of the tendon extending through the cutout is separated from a remainder of the tendon by pinching the tendon between a distal edge of the cutter and a proximal edge of the stripping tube, wherein an outer diameter of the cutter is tapered adjacent the distal edge such that the outer diameter of the cutter gradually reduces toward the distal edge of the cutter, and wherein the cutter includes a recess adjacent the distal edge of the cutter and defined by an inner diameter, wherein the inner diameter defining the recess is tapered such that the inner diameter defining the recess gradually reduces from the distal edge of the cutter moving proximally.

2. The surgical device as recited in claim 1, wherein the portion of the tendon includes a free end of the tendon.

3. A surgical device, comprising:
a shaft;
an insert adjacent a distal end of the shaft, wherein a proximal section of the insert is configured to fit within the shaft and is configured to resist rotation and axial movement of the insert relative to the shaft, wherein the insert provides a stripping tube, wherein the stripping tube includes a window permitting a portion of a tendon to enter the insert, wherein the insert includes a cutout proximal of the window and configured such that the portion of the tendon exits the insert by extending through the cutout, wherein an inner diameter of the stripping tube is circular in cross-section, wherein the stripping tube is centered about a central axis of the shaft, wherein an outer diameter of the stripping tube is tapered adjacent a distal edge of the stripping tube such that the outer diameter of the stripping tube gradually reduces toward the distal edge of the stripping tube, wherein the stripping tube defines a continuous, uninterrupted hoop; and
a cutter moveable distally to sever the tendon such that the portion of the tendon extending through the cutout is separated from a remainder of the tendon by pinching the tendon between a distal edge of the cutter and a proximal edge of the stripping tube.

4. The surgical device as recited in claim 3, wherein the proximal section of the insert includes a plurality of splines.

5. A surgical device, comprising:
a shaft;
an insert adjacent a distal end of the shaft, wherein the insert provides a stripping tube, wherein the stripping tube includes a window permitting a portion of a tendon to enter the insert, wherein the insert includes a cutout proximal of the window and configured such that the portion of the tendon exits the insert by extending through the cutout, wherein an inner diameter of the stripping tube is circular in cross-section, wherein the stripping tube provides a continuous hoop about a central axis of the shaft;
a cutter moveable distally to sever the tendon such that the portion of the tendon extending through the cutout is separated from a remainder of the tendon by pinching the tendon between a distal edge of the cutter and a proximal edge of the stripping tube, wherein an outer diameter of the cutter is tapered adjacent the distal edge such that the outer diameter of the cutter gradually reduces toward the distal edge of the cutter, wherein the cutter includes a recess adjacent the distal edge of the cutter and defined by an inner diameter, wherein the inner diameter defining the recess is tapered such that the inner diameter defining the recess gradually reduces from the distal edge of the cutter moving proximally,
wherein the surgical device includes a projection and a helical slot configured to interact such that the cutter rotates relative to the stripping tube as the cutter moves axially relative to the stripping tube, and
wherein a cap is attached to the cutter,
wherein the surgical device is configured such that the cutter moves axially when a force applied to the cap moves the cap axially,
wherein the surgical device is configured such that the cutter rotates simultaneously with the axial movement of the cutter based on the interaction of the projection and the helical slot, and
wherein the surgical device is configured such that the rotation of the cutter is not transmitted to the cap.

6. The surgical device as recited in claim 5, wherein the cutter is centered about the central axis.

7. The surgical device as recited in claim 5, wherein a distal edge of the stripping tube comprises a plurality of serrations.

8. The surgical device as recited in claim 5, wherein an outer diameter of the stripping tube is tapered adjacent the proximal edge of the stripping tube such that the outer diameter of the stripping tube gradually reduces toward the proximal edge of the stripping tube.

9. The surgical device as recited in claim 5, wherein:
the shaft projects from a handle,
the insert is attached adjacent the distal end of the shaft,
the shaft, the insert, and the handle together define a through bore extending along the central axis from a proximal end of the handle to the distal edge of the insert, and
the cutter is moveable within the through bore.

10. The surgical device as recited in claim 9, wherein the through bore exhibits a variable diameter along the central axis.

11. The surgical device as recited in claim 9, wherein:
the cutter is provided by a rod,
the rod is connected to a guide,
the guide includes the projection,
the handle includes the helical slot receiving the projection, and
the projection and helical slot interact such that movement of the rod and guide along the central axis results in rotation of the rod and guide about the central axis.

12. The surgical device as recited in claim 11, wherein:
the projection is one of a plurality of projections spaced-apart from one another about an outer surface of the guide,
the helical slot is one of a plurality of helical slots, and
each helical slot receives a corresponding one of the projections.

13. The surgical device as recited in claim 11, wherein:
the cap is attached to the guide adjacent a proximal end of the guide,
the cap is located proximal to the handle, and
the cap is configured to rotate relative to the guide.

14. The surgical device as recited in claim 9, wherein an outer contour of an end section of the handle is substantially square in cross-section with rounded corners.

15. The surgical device as recited in claim 5, wherein an outer diameter of the insert is configured to prevent rotation and axial movement of the insert relative to the shaft.

16. The surgical device as recited in claim 5, wherein the insert is formed as a separate structure from the shaft.

17. The surgical device as recited in claim 5, wherein a proximal section of the insert is configured to fit within the shaft and is configured to resist rotation and axial movement of the insert relative to the shaft.

\* \* \* \* \*